United States Patent
Belson

(10) Patent No.: US 9,421,016 B2
(45) Date of Patent: *Aug. 23, 2016

(54) APPARATUS AND METHOD FOR ENDOSCOPIC COLECTOMY

(71) Applicant: INTUITIVE SURGICAL OPERATIONS, INC., Sunnyvale, CA (US)

(72) Inventor: Amir Belson, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 145 days.

This patent is subject to a terminal disclaimer.

(21) Appl. No.: 14/199,220

(22) Filed: Mar. 6, 2014

(65) Prior Publication Data

US 2014/0188142 A1    Jul. 3, 2014

Related U.S. Application Data

(60) Continuation of application No. 13/729,602, filed on Dec. 28, 2012, now Pat. No. 8,696,694, which is a division of application No. 12/027,739, filed on Feb. 7, 2008, now Pat. No. 8,361,090, which is a division of (Continued)

(51) Int. Cl.
*A61B 17/11* (2006.01)
*A61B 1/00* (2006.01)
(Continued)

(52) U.S. Cl.
CPC ........... *A61B 17/1114* (2013.01); *A61B 1/0055* (2013.01); *A61B 1/00147* (2013.01);
(Continued)

(58) Field of Classification Search
CPC ................. A61B 17/1114; A61B 17/22032; A61B 2017/1117; A61B 2017/1103; A61B 2017/22034; A61B 2017/22054; A61B 2017/111; A61B 2017/0269

See application file for complete search history.

(56) References Cited

U.S. PATENT DOCUMENTS 616,672 A    12/1898  Kelling
2,510,198 A   6/1950  Tesmer
(Continued)

FOREIGN PATENT DOCUMENTS

DE    2823025 A1   12/1979
DE    3707787 A1    9/1988
(Continued)

OTHER PUBLICATIONS

Berger, W. L. et al., "Sigmoid Stiffener for Decompression Tube Placement in Colonic Pseudo-Obstruction," Endoscopy, 2000, vol. 32, Issue 1, pp. 54-57.

(Continued)

*Primary Examiner* — Darwin Erezo
*Assistant Examiner* — Shaun L David

(57) ABSTRACT

Apparatus and methods for endoscopic colectomy are described herein. A colectomy device having a first and a second tissue approximation device is mounted on a colonoscope separated from one another. During deployment of the colectomy device, a diseased portion of the colon is positioned inbetween the tissue approximation devices. The tissue approximation devices are radially expanded such that they contact and grasp the colon wall at two sites adjacent to the diseased portion of the colon. The diseased portion is separated from the omentum and is transected using a laparoscope or is drawn into the colonoscope for later removal. The tissue approximation devices are then urged towards one another over the colonoscope to approximate the two free edges of the colon into contact together where they are fastened to one another using the tissue approximation device as a surgical stapler to create an end-to-end anastomosis.

20 Claims, 19 Drawing Sheets

Related U.S. Application Data application No. 10/327,370, filed on Dec. 20, 2002, now Pat. No. 7,338,505.

(60) Provisional application No. 60/347,674, filed on Jan. 9, 2002.

(51) Int. Cl.
  *A61B 1/005* (2006.01)
  *A61B 1/31* (2006.01)
  *A61B 17/00* (2006.01)
  *A61B 17/22* (2006.01)

(52) U.S. Cl.
  CPC .............. *A61B 1/31* (2013.01); *A61B 1/0058* (2013.01); *A61B 2017/003* (2013.01); *A61B 2017/00557* (2013.01); *A61B 2017/1103* (2013.01); *A61B 2017/22034* (2013.01); *A61B 2017/22054* (2013.01)

(56) References Cited

U.S. PATENT DOCUMENTS

| | | | |
|---|---|---|---|
| 2,533,494 A | 12/1950 | Mitchell, Jr. | |
| 2,767,705 A | 10/1956 | Moore | |
| 3,060,972 A | 10/1962 | Sheldon | |
| 3,071,161 A | 1/1963 | Ulrich | |
| 3,096,962 A | 7/1963 | Meijs | |
| 3,162,214 A | 12/1964 | Wilfred, Jr. | |
| 3,168,274 A | 2/1965 | Street | |
| 3,190,286 A | 6/1965 | Stokes | |
| 3,266,059 A | 8/1966 | Stelle | |
| 3,430,662 A | 3/1969 | Guarnaschelli | |
| 3,497,083 A | 2/1970 | Anderson | |
| 3,546,961 A | 12/1970 | Marton | |
| 3,610,231 A | 10/1971 | Takahashi et al. | |
| 3,625,084 A | 12/1971 | Siebert | |
| 3,643,653 A | 2/1972 | Takahashi et al. | |
| 3,739,770 A | 6/1973 | Mori | |
| 3,773,034 A | 11/1973 | Burns et al. | |
| 3,780,740 A | 12/1973 | Rhea | |
| 3,858,578 A | 1/1975 | Milo | |
| 3,871,358 A | 3/1975 | Fukuda et al. | |
| 3,897,775 A | 8/1975 | Furihata | |
| 3,913,565 A | 10/1975 | Kawahara | |
| 3,946,727 A | 3/1976 | Okada et al. | |
| 3,990,434 A | 11/1976 | Free | |
| 4,054,128 A | 10/1977 | Seufert et al. | |
| 4,176,662 A | 12/1979 | Frazer | |
| 4,198,982 A | 4/1980 | Fortner et al. | |
| 4,233,981 A | 11/1980 | Schomacher | |
| 4,236,509 A | 12/1980 | Takahashi et al. | |
| 4,240,435 A | 12/1980 | Yazawa et al. | |
| 4,273,111 A | 6/1981 | Tsukaya | |
| 4,327,711 A | 5/1982 | Takagi | |
| 4,366,810 A | 1/1983 | Slanetz, Jr. | |
| 4,393,728 A | 7/1983 | Larson et al. | |
| 4,432,349 A | 2/1984 | Oshiro | |
| 4,483,326 A | 11/1984 | Yamaka et al. | |
| 4,489,826 A | 12/1984 | Dubson | |
| 4,494,417 A | 1/1985 | Larson et al. | |
| 4,499,895 A | 2/1985 | Takayama | |
| 4,503,842 A | 3/1985 | Takayama | |
| 4,543,090 A | 9/1985 | McCoy | |
| 4,551,061 A | 11/1985 | Olenick | |
| 4,559,928 A | 12/1985 | Takayama | |
| 4,566,843 A | 1/1986 | Iwatsuka et al. | |
| 4,577,621 A | 3/1986 | Patel | |
| 4,592,341 A | 6/1986 | Omagari et al. | |
| 4,592,354 A | 6/1986 | Rothfuss | |
| 4,601,283 A | 7/1986 | Chikama | |
| 4,601,713 A | 7/1986 | Fuqua | |
| 4,621,618 A | 11/1986 | Omagari | |
| 4,624,243 A | 11/1986 | Lowery et al. | |
| 4,630,649 A | 12/1986 | Oku | |
| 4,643,184 A | 2/1987 | Mobin-Uddin | |
| 4,646,722 A | 3/1987 | Silverstein et al. | |
| 4,648,733 A | 3/1987 | Merkt | |
| 4,651,718 A | 3/1987 | Collins et al. | |
| 4,655,257 A | 4/1987 | Iwashita | |
| 4,683,773 A | 8/1987 | Diamond | |
| 4,686,963 A | 8/1987 | Cohen et al. | |
| 4,712,969 A | 12/1987 | Kimura | |
| 4,726,355 A | 2/1988 | Okada | |
| 4,753,222 A | 6/1988 | Morishita | |
| 4,753,223 A | 6/1988 | Bremer | |
| 4,754,909 A | 7/1988 | Barker et al. | |
| 4,784,117 A | 11/1988 | Miyazaki | |
| 4,787,369 A | 11/1988 | Allred, III et al. | |
| 4,788,967 A | 12/1988 | Ueda | |
| 4,793,326 A | 12/1988 | Shishido | |
| 4,796,607 A | 1/1989 | Allred, III et al. | |
| 4,799,474 A | 1/1989 | Ueda | |
| 4,800,890 A | 1/1989 | Cramer | |
| 4,807,593 A | 2/1989 | Ito | |
| 4,815,450 A | 3/1989 | Patel | |
| 4,832,473 A | 5/1989 | Ueda | |
| 4,834,068 A | 5/1989 | Gottesman | |
| 4,873,965 A | 10/1989 | Danieli | |
| 4,873,990 A | 10/1989 | Holmes et al. | |
| 4,879,991 A | 11/1989 | Ogiu | |
| 4,884,557 A | 12/1989 | Takehana et al. | |
| 4,890,602 A | 1/1990 | Hake | |
| 4,895,431 A | 1/1990 | Tsujiuchi et al. | |
| 4,899,731 A | 2/1990 | Takayama et al. | |
| 4,904,048 A | 2/1990 | Sogawa et al. | |
| 4,917,114 A | 4/1990 | Green et al. | |
| 4,919,112 A | 4/1990 | Siegmund | |
| 4,930,494 A | 6/1990 | Takehana et al. | |
| 4,949,927 A | 8/1990 | Madocks et al. | |
| 4,957,486 A | 9/1990 | Davis | |
| 4,969,709 A | 11/1990 | Sogawa et al. | |
| 4,971,035 A | 11/1990 | Ito | |
| 4,977,886 A | 12/1990 | Takehana et al. | |
| 4,977,887 A | 12/1990 | Gouda | |
| 4,987,314 A | 1/1991 | Gotanda et al. | |
| 5,005,558 A | 4/1991 | Aomori | |
| 5,005,559 A | 4/1991 | Blanco et al. | |
| 5,014,709 A | 5/1991 | Bjelkhagen et al. | |
| 5,018,509 A | 5/1991 | Suzuki et al. | |
| 5,025,778 A | 6/1991 | Silverstein et al. | |
| 5,060,632 A | 10/1991 | Hibino et al. | |
| 5,092,901 A | 3/1992 | Hunter et al. | |
| 5,122,156 A | 6/1992 | Granger et al. | |
| 5,125,395 A | 6/1992 | Adair | |
| 5,127,393 A | 7/1992 | McFarlin et al. | |
| 5,159,446 A | 10/1992 | Hibino et al. | |
| 5,166,787 A | 11/1992 | Irion | |
| 5,174,276 A | 12/1992 | Crockard | |
| 5,174,277 A | 12/1992 | Matsumaru | |
| 5,188,111 A | 2/1993 | Yates et al. | |
| 5,207,695 A | 5/1993 | Trout, III | |
| 5,217,001 A | 6/1993 | Nakao et al. | |
| 5,220,911 A | 6/1993 | Tamura | |
| 5,228,429 A | 7/1993 | Hatano | |
| 5,234,448 A | 8/1993 | Wholey et al. | |
| 5,243,967 A | 9/1993 | Hibino | |
| 5,250,058 A | 10/1993 | Miller et al. | |
| 5,251,611 A | 10/1993 | Zehel et al. | |
| 5,253,647 A | 10/1993 | Takahashi et al. | |
| 5,254,127 A * | 10/1993 | Wholey | A61B 17/11 285/397 |
| 5,254,809 A | 10/1993 | Martin | |
| 5,257,617 A | 11/1993 | Takahashi | |
| 5,259,364 A | 11/1993 | Bob et al. | |
| 5,271,381 A | 12/1993 | Ailinger et al. | |
| 5,271,382 A | 12/1993 | Chikama | |
| 5,279,610 A | 1/1994 | Park et al. | |
| 5,282,810 A * | 2/1994 | Allen | A61B 17/115 606/150 |
| 5,297,443 A | 3/1994 | Wentz | |
| 5,309,927 A | 5/1994 | Welch | |
| 5,314,435 A | 5/1994 | Green et al. | |
| 5,325,845 A | 7/1994 | Adair | |

(56) References Cited

U.S. PATENT DOCUMENTS

| | | |
|---|---|---|
| 5,337,732 A | 8/1994 | Grundfest et al. |
| 5,337,733 A | 8/1994 | Bauerfeind et al. |
| 5,343,874 A | 9/1994 | Picha et al. |
| 5,347,987 A | 9/1994 | Feldstein et al. |
| 5,348,259 A | 9/1994 | Blanco et al. |
| 5,364,389 A | 11/1994 | Anderson |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,395,030 A * | 3/1995 | Kuramoto ......... A61B 1/00087 227/179.1 |
| 5,400,769 A | 3/1995 | Tanii et al. |
| 5,402,768 A | 4/1995 | Adair |
| 5,411,508 A | 5/1995 | Bessler et al. |
| 5,413,108 A | 5/1995 | Alfano |
| 5,421,337 A | 6/1995 | Richards-Kortum et al. |
| 5,425,738 A * | 6/1995 | Gustafson ......... A61B 17/1114 606/151 |
| 5,429,118 A | 7/1995 | Cole et al. |
| 5,439,000 A | 8/1995 | Gunderson et al. |
| 5,451,221 A | 9/1995 | Cho et al. |
| 5,456,714 A | 10/1995 | Owen |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,489,256 A | 2/1996 | Adair |
| 5,503,635 A | 4/1996 | Sauer et al. |
| 5,507,287 A | 4/1996 | Palcic et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,586,968 A | 12/1996 | Grundl et al. |
| 5,590,660 A | 1/1997 | MacAulay et al. |
| 5,601,087 A | 2/1997 | Gunderson et al. |
| 5,602,449 A | 2/1997 | Krause et al. |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,651,769 A | 7/1997 | Waxman et al. |
| 5,653,690 A | 8/1997 | Booth et al. |
| 5,658,238 A | 8/1997 | Suzuki et al. |
| 5,662,585 A | 9/1997 | Willis et al. |
| 5,662,587 A | 9/1997 | Grundfest et al. |
| 5,665,050 A | 9/1997 | Benecke |
| 5,667,476 A | 9/1997 | Frassica et al. |
| 5,669,918 A * | 9/1997 | Balazs ................ A61B 17/115 227/176.1 |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,762,613 A | 6/1998 | Sutton et al. |
| 5,765,561 A | 6/1998 | Chen et al. |
| 5,769,792 A | 6/1998 | Palcic et al. |
| 5,772,597 A | 6/1998 | Goldberger et al. |
| 5,773,835 A | 6/1998 | Sinofsky |
| 5,779,624 A | 7/1998 | Chang |
| 5,807,241 A | 9/1998 | Heimberger |
| 5,810,715 A | 9/1998 | Moriyama |
| 5,810,716 A | 9/1998 | Mukherjee et al. |
| 5,810,717 A | 9/1998 | Maeda et al. |
| 5,810,776 A | 9/1998 | Bacich et al. |
| 5,813,976 A | 9/1998 | Filipi et al. |
| 5,827,190 A | 10/1998 | Palcic et al. |
| 5,827,265 A | 10/1998 | Glinsky et al. |
| 5,839,639 A | 11/1998 | Sauer et al. |
| 5,842,973 A | 12/1998 | Bullard |
| 5,860,581 A | 1/1999 | Robertson et al. |
| 5,860,914 A | 1/1999 | Chiba et al. |
| 5,868,760 A | 2/1999 | McGuckin, Jr. |
| 5,876,329 A | 3/1999 | Harhen |
| 5,876,373 A | 3/1999 | Giba et al. |
| 5,885,208 A | 3/1999 | Moriyama |
| 5,893,369 A | 4/1999 | LeMole |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,941,908 A | 8/1999 | Goldsteen et al. |
| 5,957,833 A | 9/1999 | Shan |
| 5,968,052 A | 10/1999 | Sullivan, III |
| 5,971,767 A | 10/1999 | Kaufman et al. |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,993,447 A | 11/1999 | Blewett et al. |
| 5,996,346 A | 12/1999 | Maynard |
| 6,016,440 A | 1/2000 | Simon et al. |
| 6,033,359 A | 3/2000 | Doi |
| 6,036,636 A | 3/2000 | Motoki et al. |
| 6,036,702 A | 3/2000 | Bachinski et al. |
| 6,042,155 A | 3/2000 | Lockwood |
| 6,048,307 A | 4/2000 | Grundl et al. |
| 6,063,022 A | 5/2000 | Ben-Haim |
| 6,066,102 A | 5/2000 | Townsend et al. |
| 6,066,132 A | 5/2000 | Chen et al. |
| 6,068,638 A | 5/2000 | Makower |
| 6,096,289 A | 8/2000 | Goldenberg |
| 6,099,464 A | 8/2000 | Shimizu et al. |
| 6,099,465 A | 8/2000 | Inoue |
| 6,099,485 A | 8/2000 | Patterson |
| 6,106,510 A | 8/2000 | Lunn et al. |
| 6,117,148 A | 9/2000 | Ravo et al. |
| 6,119,913 A | 9/2000 | Adams et al. |
| 6,129,667 A | 10/2000 | Dumoulin et al. |
| 6,129,683 A | 10/2000 | Sutton et al. |
| 6,141,577 A | 10/2000 | Rolland et al. |
| 6,149,581 A | 11/2000 | Klingenstein |
| 6,162,171 A | 12/2000 | Ng et al. |
| 6,174,280 B1 | 1/2001 | Oneda et al. |
| 6,174,291 B1 | 1/2001 | McMahon et al. |
| 6,179,776 B1 | 1/2001 | Adams et al. |
| 6,185,448 B1 | 2/2001 | Borovsky |
| 6,201,989 B1 | 3/2001 | Whitehead et al. |
| 6,203,493 B1 | 3/2001 | Ben-Haim |
| 6,203,494 B1 | 3/2001 | Moriyama |
| 6,210,337 B1 | 4/2001 | Dunham et al. |
| 6,221,006 B1 | 4/2001 | Dubrul et al. |
| 6,241,657 B1 | 6/2001 | Chen et al. |
| 6,249,076 B1 | 6/2001 | Madden et al. |
| 6,264,086 B1 | 7/2001 | McGuckin, Jr. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,319,197 B1 | 11/2001 | Tsuji et al. |
| 6,327,492 B1 | 12/2001 | Lemelson |
| 6,332,089 B1 | 12/2001 | Acker et al. |
| 6,348,058 B1 | 2/2002 | Melkent et al. |
| 6,366,799 B1 | 4/2002 | Acker et al. |
| 6,402,687 B1 | 6/2002 | Ouchi |
| 6,408,889 B1 | 6/2002 | Komachi |
| 6,428,203 B1 | 8/2002 | Danley |
| 6,443,888 B1 | 9/2002 | Ogura et al. |
| 6,453,190 B1 | 9/2002 | Acker et al. |
| 6,459,481 B1 | 10/2002 | Schaack |

(56) References Cited

U.S. PATENT DOCUMENTS

| | | |
|---|---|---|
| 6,468,203 B2 | 10/2002 | Belson |
| 6,482,149 B1 | 11/2002 | Torii |
| 6,485,413 B1 | 11/2002 | Boppart et al. |
| 6,485,496 B1 | 11/2002 | Suyker et al. |
| 6,490,467 B1 | 12/2002 | Bucholz et al. |
| 6,503,259 B2 | 1/2003 | Huxel et al. |
| 6,511,417 B1 | 1/2003 | Taniguchi et al. |
| 6,511,418 B2 | 1/2003 | Shahidi et al. |
| 6,517,477 B1 | 2/2003 | Wendlandt |
| 6,527,706 B2 | 3/2003 | Ide |
| 6,537,211 B1 | 3/2003 | Wang et al. |
| 6,544,215 B1 | 4/2003 | Bencini et al. |
| 6,554,793 B1 | 4/2003 | Pauker et al. |
| 6,569,173 B1 | 5/2003 | Blatter et al. |
| 6,616,600 B2 | 9/2003 | Pauker |
| 6,638,213 B2 | 10/2003 | Ogura et al. |
| 6,641,528 B2 | 11/2003 | Torii |
| 6,656,110 B1 | 12/2003 | Irion et al. |
| 6,666,873 B1 * | 12/2003 | Cassell ............ A61B 17/0643 606/153 |
| 6,699,183 B1 | 3/2004 | Wimmer |
| 6,736,822 B2 * | 5/2004 | McClellan ....... A61B 17/12009 606/139 |
| 6,743,239 B1 | 6/2004 | Kuehn et al. |
| 6,761,685 B2 | 7/2004 | Adams et al. |
| 6,800,056 B2 | 10/2004 | Tartaglia et al. |
| 6,808,499 B1 | 10/2004 | Churchill et al. |
| 6,808,520 B1 | 10/2004 | Fourkas et al. |
| 6,817,973 B2 | 11/2004 | Merril et al. |
| 6,837,846 B2 | 1/2005 | Jaffe et al. |
| 6,837,849 B2 | 1/2005 | Ogura et al. |
| 6,843,793 B2 | 1/2005 | Brock et al. |
| 6,850,794 B2 | 2/2005 | Shahidi |
| 6,858,005 B2 | 2/2005 | Ohline et al. |
| 6,869,396 B2 | 3/2005 | Belson |
| 6,875,170 B2 | 4/2005 | Francois et al. |
| 6,890,297 B2 | 5/2005 | Belson |
| 6,902,528 B1 | 6/2005 | Garibaldi et al. |
| 6,960,161 B2 | 11/2005 | Amling et al. |
| 6,974,411 B2 | 12/2005 | Belson |
| 6,984,203 B2 | 1/2006 | Tartaglia et al. |
| 7,018,331 B2 | 3/2006 | Chang et al. |
| 7,087,013 B2 | 8/2006 | Belson et al. |
| 7,338,505 B2 | 3/2008 | Belson |
| 8,182,418 B2 | 5/2012 | Durant et al. |
| 8,361,090 B2 | 1/2013 | Belson |
| 2002/0016607 A1 | 2/2002 | Bonadio et al. |
| 2002/0062062 A1 | 5/2002 | Belson et al. |
| 2002/0082625 A1 * | 6/2002 | Huxel ............... A61B 17/0643 606/153 |
| 2002/0091398 A1 * | 7/2002 | Galdonik ........... A61B 17/11 606/153 |
| 2002/0120254 A1 | 8/2002 | Julian et al. |
| 2002/0147385 A1 | 10/2002 | Butler et al. |
| 2002/0151767 A1 | 10/2002 | Sonnenschein et al. |
| 2002/0169361 A1 | 11/2002 | Taniguchi et al. |
| 2002/0193662 A1 | 12/2002 | Belson |
| 2003/0045778 A1 * | 3/2003 | Ohline ............... A61B 1/0053 600/114 |
| 2003/0083550 A1 | 5/2003 | Miyagi |
| 2003/0130598 A1 | 7/2003 | Manning et al. |
| 2003/0167007 A1 | 9/2003 | Belson |
| 2003/0195387 A1 | 10/2003 | Kortenbach et al. |
| 2003/0236505 A1 | 12/2003 | Bonadio et al. |
| 2003/0236549 A1 | 12/2003 | Bonadio et al. |
| 2004/0019254 A1 | 1/2004 | Belson et al. |
| 2004/0106852 A1 | 6/2004 | Windheuser et al. |
| 2004/0176683 A1 | 9/2004 | Whitin et al. |
| 2004/0193008 A1 | 9/2004 | Jaffe et al. |
| 2004/0193009 A1 | 9/2004 | Jaffe et al. |
| 2004/0210109 A1 | 10/2004 | Jaffe et al. |
| 2004/0220450 A1 | 11/2004 | Jaffe et al. |
| 2005/0020901 A1 | 1/2005 | Belson et al. |
| 2005/0085693 A1 | 4/2005 | Belson et al. |
| 2005/0124855 A1 | 6/2005 | Jaffe et al. |
| 2005/0154258 A1 | 7/2005 | Tartaglia et al. |
| 2005/0154261 A1 | 7/2005 | Ohline et al. |
| 2005/0165276 A1 | 7/2005 | Belson et al. |
| 2005/0203339 A1 | 9/2005 | Butler et al. |
| 2005/0209506 A1 | 9/2005 | Butler et al. |
| 2005/0209509 A1 | 9/2005 | Belson |
| 2005/0222497 A1 | 10/2005 | Belson |
| 2005/0222498 A1 | 10/2005 | Belson |
| 2006/0009678 A1 | 1/2006 | Jaffe et al. |
| 2006/0052664 A1 | 3/2006 | Julian et al. |
| 2006/0235457 A1 | 10/2006 | Belson |
| 2006/0235458 A1 | 10/2006 | Belson |
| 2006/0258912 A1 | 11/2006 | Belson et al. |
| 2007/0043259 A1 | 2/2007 | Jaffe et al. |
| 2007/0093858 A1 | 4/2007 | Gambale et al. |
| 2007/0135803 A1 | 6/2007 | Belson |
| 2007/0161291 A1 | 7/2007 | Swinehart et al. |
| 2007/0161857 A1 | 7/2007 | Durant et al. |
| 2007/0249901 A1 | 10/2007 | Ohline et al. |
| 2007/0270650 A1 | 11/2007 | Eno et al. |
| 2008/0045794 A1 | 2/2008 | Belson |
| 2013/0116712 A1 | 5/2013 | Belson |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 165718 A2 | 12/1985 |
| EP | 382974 A1 | 8/1990 |
| EP | 497781 B1 | 1/1994 |
| EP | 0993804 A1 | 4/2000 |
| EP | 1101442 A2 | 5/2001 |
| FR | 2732225 A1 | 10/1996 |
| GB | 2347685 A | 9/2000 |
| JP | 63136014 A2 | 6/1988 |
| JP | 63272322 A2 | 11/1988 |
| JP | 1152413 A2 | 6/1989 |
| JP | 1229220 A2 | 9/1989 |
| JP | 1262372 A2 | 10/1989 |
| JP | 2246986 A2 | 10/1990 |
| JP | 2296209 A2 | 12/1990 |
| JP | 3136630 A2 | 6/1991 |
| JP | 4054970 A2 | 2/1992 |
| JP | 5011196 A2 | 1/1993 |
| JP | 5111458 A2 | 5/1993 |
| JP | 5305073 A2 | 11/1993 |
| JP | 6007287 A2 | 1/1994 |
| JP | 8322786 A2 | 12/1996 |
| JP | 9028662 A2 | 2/1997 |
| JP | 10337274 A2 | 12/1998 |
| JP | 11042258 A2 | 2/1999 |
| JP | 21046318 A2 | 2/2001 |
| SU | 871786 A1 | 10/1981 |
| SU | 1256955 A1 | 9/1986 |
| SU | 1301701 A1 | 4/1987 |
| WO | WO-9317751 A1 | 9/1993 |
| WO | WO-9419051 A1 | 9/1994 |
| WO | WO-9504556 A2 | 2/1995 |
| WO | WO-9509562 A1 | 4/1995 |
| WO | WO-9605768 A1 | 2/1996 |
| WO | WO-9710746 A1 | 3/1997 |
| WO | WO-9725101 A2 | 7/1997 |
| WO | WO-9729701 A1 | 8/1997 |
| WO | WO-9729710 A1 | 8/1997 |
| WO | WO-9824017 A2 | 6/1998 |
| WO | WO-9849938 A1 | 11/1998 |
| WO | WO-9916359 A1 | 4/1999 |
| WO | WO-9933392 A1 | 7/1999 |
| WO | WO-9951283 A2 | 10/1999 |
| WO | WO-9959664 A1 | 11/1999 |
| WO | WO-0010456 A1 | 3/2000 |
| WO | WO-0027462 A1 | 5/2000 |
| WO | WO-0054653 A1 | 9/2000 |
| WO | WO-0074565 A1 | 12/2000 |
| WO | WO-0149353 A2 | 7/2001 |
| WO | WO-0167964 A2 | 9/2001 |
| WO | WO-0170096 A1 | 9/2001 |
| WO | WO-0170097 A1 | 9/2001 |

(56) References Cited

FOREIGN PATENT DOCUMENTS

| WO | WO-0174235 A1 | 10/2001 |
|---|---|---|
| WO | WO-0180935 A1 | 11/2001 |
| WO | WO-0239909 A1 | 5/2002 |
| WO | WO-0247549 A1 | 6/2002 |
| WO | WO-02064028 A1 | 8/2002 |
| WO | WO-02068988 A1 | 9/2002 |
| WO | WO-02069841 A2 | 9/2002 |
| WO | WO-02089692 A1 | 11/2002 |
| WO | WO-02096276 A1 | 12/2002 |
| WO | WO-03028547 A2 | 4/2003 |
| WO | WO-2004019769 A1 | 3/2004 |
| WO | WO-2004084702 A2 | 10/2004 |

OTHER PUBLICATIONS

Hasson, H.M., "Technique of Open Laparoscopy," (from step 1 to step 9), May 1979, 2424 North Clark Street, Chicago, Illinois 60614, 3 pages.

International Search Report for Application No. PCT/US2002/041358, mailed on Jul. 17, 2003, 1 page.

Ireland Application No. 2000/0225 filed on Mar. 22, 2000, Inventor Declan B., et al.

Ireland Application No. 2000/0559 filed on Jul. 11, 2000, Inventor Declan B., et al.

Lee, Thomas S. et al., "A highly redundant robot system for inspection," Proceedings of Conference on Intelligent Robotics in Field, Factory, Service, and Space (CIRFFSS '94). Mar. 21-24, 1994. vol. 1, pp. 142-148. Houston, Texas.

McKernan, J.B. et al., "Laparoscopic general surgery," Journal of the Medical Association of Georgia, Mar. 1990, vol. 79, Issue 3, pp. 157-159.

Slatkin, A.B. et al., "The development of a robotic endoscope," Proceedings 1995 IEEE/RSJ International Conference on Intelligent Robots and Systems, Aug. 5-9, 1995, vol. 2, pp. 162-171, Pittsburgh, Pennsylvania.

Supplementary European Search Report for Application No. EP02794411, mailed on Feb. 22, 2008, 3 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Woodley et al., U.S. Appl. No. 11/871,104 entitled "System for managing bowden cables in articulating instruments," filed Oct. 11, 2007.

\* cited by examiner

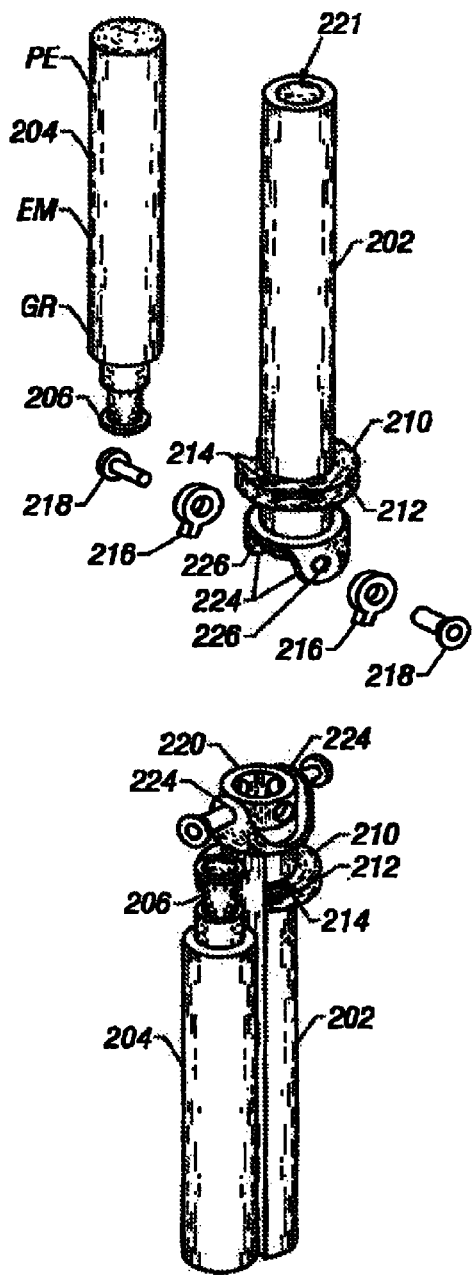
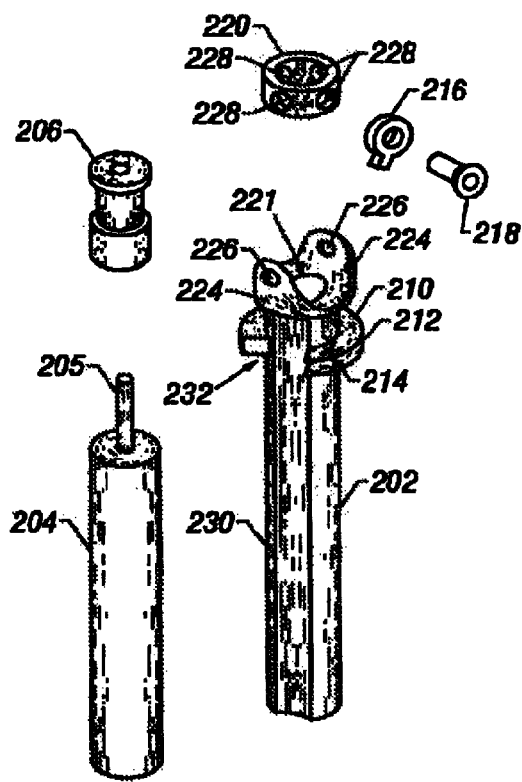
FIG. 13A
FIG. 13B

FIG. 15B
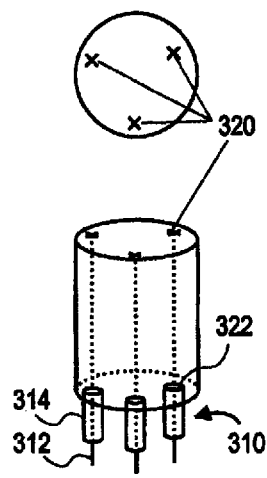
FIG. 15C
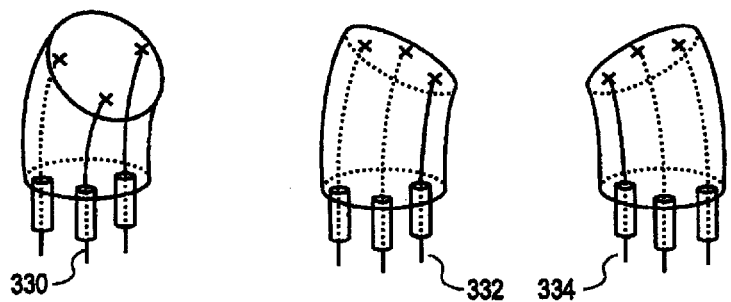
FIG. 15D   FIG. 15E   FIG. 15F

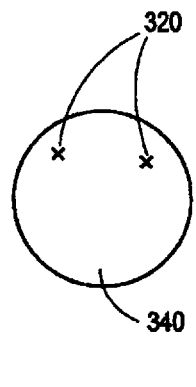
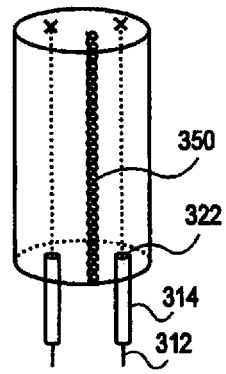
FIG. 16A  FIG. 16B
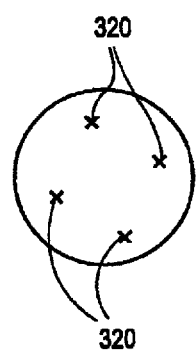
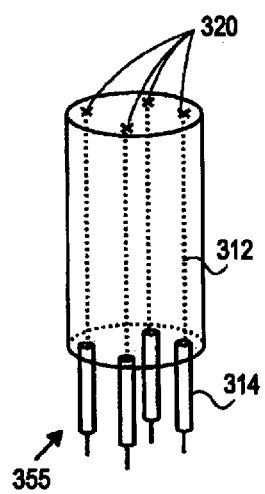
FIG. 16C  FIG. 16D

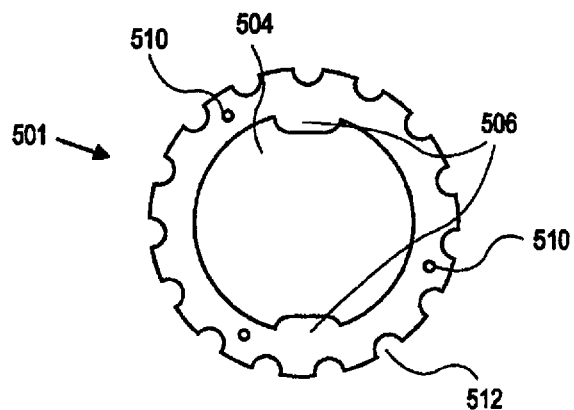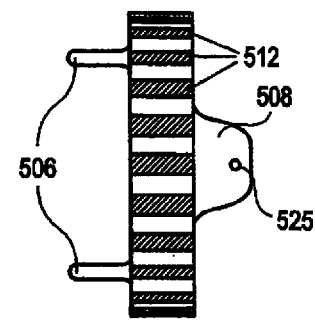
FIG. 18A    FIG. 18B
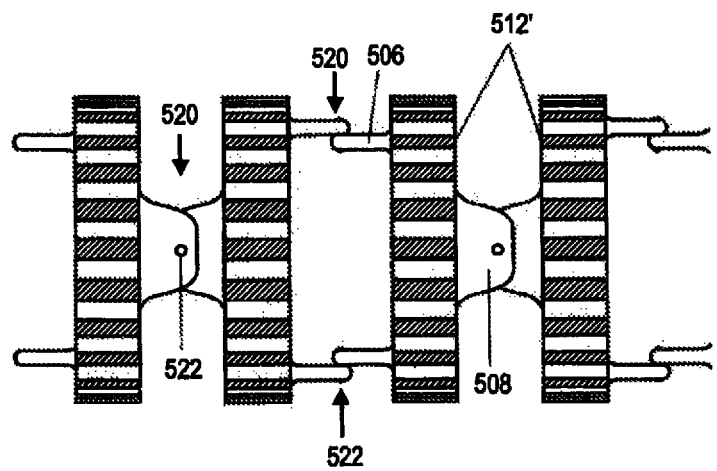
FIG. 18C

APPARATUS AND METHOD FOR ENDOSCOPIC COLECTOMY

CROSS REFERENCE TO RELATED APPLICATIONS

This application is a continuation application of U.S. patent application Ser. No. 13/729,602 (filed Dec. 28, 2012), which is a divisional application of U.S. patent application Ser. No. 12/027,739 (filed Feb. 7, 2008; now U.S. Pat. No. 8,361,090 B2), which is a divisional application of U.S. patent application Ser. No. 10/327,370 (filed Dec. 20, 2002; now U.S. Pat. No. 7,338,505 B2), which claims the benefit of priority of U.S. Provisional Patent Application No. 60/347,674 (filed Jan. 9, 2002), which are all incorporated herein by reference in their entirety.

FIELD OF THE INVENTION

The present invention relates generally to surgical methods and apparatus. More particularly, it relates to methods and apparatus for performing endoscopic colectomy.

BACKGROUND OF THE INVENTION

Endoscopy studies the intraluminal aspects of hollow organs of the upper and lower intestine including the esophagus, stomach and the colon through cannulation of the lumen via the mouth or anus. Endoscopic polypectomy is presently limited to a submucosal resection. The endoscopist is often unable to completely resect a sessile polyp or lesion and therefore the patient is subjected to subsequent definitive surgery, i.e. resection of the base of the tumor. Endoscopic polypectomy can be used to debulk sessile masses but it is unable to resect mural disease. Incomplete resection of a sessile polyp may destroy the biopsy specimen and alter the relationship of the gross specimen given to the pathologist thereby resulting in the pathologist possibly providing incorrect or incomplete study results. The endoscopist is also unable to correct uncommon, but life threatening, procedural complications such as perforations. Other cases where resection is required are invasive tumors, perforation from different causes, inflammatory bowel disease, diverticulosis and others.

Surgical approaches for resecting diseased tissue are largely practiced by making large laparotomy incisions or using minimally invasive techniques such as laparoscopic surgery in which tissues are resected and repaired through small incisions.

There are numerous surgical devices enabling surgeons to resect diseased tissue and subsequently anastomose remaining tissue either through a conventional incision or using a laparoscope and making one or more relatively small incisions. Additionally, endoscopically assisted stapling devices are known which enable surgeons to remotely anastomose lumenal structures such as the bowel. Endoscopically assisted bowel anastomosis nevertheless typically requires extralumenal assistance via a traditional laparotomy incision or use of a laparoscope.

Trends in surgery are towards minimally invasive procedures as evidenced by developments including laparoscopic cholecystectomy, laparoscopic appendectomy and laparoscopically assisted partial colectomies and hernia repairs. All of these minimally invasive procedures involve introducing a laparoscope through the abdominal wall and creating other associated openings to gain access to the peritoneal cavity in order to perform the necessary surgical procedure. Typically, general anesthesia is required. Endoscopically possible procedures include polypectomy, mucosectomy, and cauterization. During "laparoscopic colectomy" today the colon is separated from its omentum laparoscopically and then the colon is exteriorized out of the abdominal cavity, through a laparotomy incision where the resection and anastomosis are performed extracorporeally.

Disadvantages of the laparoscopic method include the need to traverse the abdominal wall, increased operating time secondary to the lack of exposure for the procedure and possibly the need to convert to an "open" laparotomy in the course of performing the procedure.

Present stapling techniques in surgery are for the most part functionally adequate but limited. Devices exist including the GIA and EEA staplers which can be used to transect tissue in a linear or circular fashion, respectively, with subsequent anastomosis with staples. The linear GIA is relatively versatile. The EEA is primarily suited for lower colonic circular anastomosis after a lesion has been surgically removed (via laparotomy or laparoscopically) or during a colostomy takedown procedure.

The rigid post of the EEA stapler severely limits its use, as well as requiring that an open procedure be utilized. The steerable endoscopic stapler is useful in allowing for more bowel accessibility; however, it remains dependent upon transabdominal surgical exposure prior to utilization. While laparoscopic surgical instruments have been used for bowel anastomosis, in such procedures the bowel is exteriorized through the laparoscopic incision and anastomosed extracorporeally or in an augmented stapled side-to-side fashion.

U.S. Pat. Nos. 5,868,760 and 6,264,086 describe a method and apparatus for performing endolumenal resection of tissue, in particular for removal of diseased portions of a patient's colon. This purely endolumenal approach to colostomy does not fully address the surgical anatomy of the colon. As is well known, the colon and other viscera are connected and supported within the abdomen by the omentum, a membranous extension of the peritoneum that carries the blood supply to the colon. Resection of more than a small portion of the colon requires mobilization of the colon from the omentum and ligation or cauterization of the blood vessels supplying that portion of the colon. This aspect is not addressed by the endolumenal approach described; therefore it would be suitable for resecting only small portions of the colon.

Commonly owned and copending U.S. patent application Ser. No. 09/790,204 filed Feb. 20, 2001 (now U.S. Pat. No. 6,468,203); Ser. No. 09/969,927 filed Oct. 2, 2001; and Ser. No. 10/229,577 filed Aug. 27, 2002, describe steerable colonoscopes that uses serpentine motion to facilitate rapid and safe insertion of the colonoscope into a patient's colon. The technology described therein can also be used in conjunction with the methods and apparatus of the present invention to facilitate endoscopic colectomy or resection of any other part of the gastrointestinal system including, but not limited to, the esophagus, duodenum, jejunum and ileum or any other tubular organ like the bronchus. These patents and patent applications, and all other patents and patent applications referred to herein, are hereby incorporated by reference in their entirety.

SUMMARY OF THE INVENTION

In keeping with the foregoing discussion, the present invention takes the form of methods and apparatus for performing endoscopic colectomy that combine the advantages of the laparoscopic and endolumenal approaches. The diseased portion of the colon to be resected is identified using either laparoscopic and/or colonoscopic techniques or using another imaging modality. A colectomy device mounted on a colonoscope grasps the colon wall at two sites adjacent to a diseased portion of the colon. Using laparoscopic techniques, the diseased portion of the colon is separated from the omentum and the blood vessels supplying it are ligated or cauterized. The colon wall is transected to remove the diseased portion and the excised tissue is removed using the laparoscope or drawn into the colectomy device for later removal upon withdrawal of the colonoscope. The colectomy device approximates the two ends of the colon and performs an end-to-end anastomosis. If the part to be resected is a tumor, prior to the resection, the edges of the segment to be resected will be stapled to seal it and prevent spillage of malignant cells to the healthy tissue.

The methods and apparatus of the present invention provide a number of benefits not realized by the prior art approaches to colectomy. As stated above, the purely endolumenal approach does not provide for separation of the colon from the omentum, which is necessary when resecting more than just a small portion of the colon wall. By combining laparoscopic techniques with a colonoscope-mounted colectomy device, the present invention overcomes this deficiency in the prior art allowing a more comprehensive approach to colectomy. Unlike prior art laparoscopic techniques, however, the colon does not need to be exteriorized for excision of the diseased portion or anastomosis of the remaining colon. The colonoscope-mounted colectomy device approximates the ends of the colon and performs an anastomosis from the interior of the lumen of the colon. The excised tissue can be drawn into the colectomy device for removal through the lumen of the colon along with the colonoscope or can be taken out by the laparoscope, which can be done through a very small incision in the patient's skin. The prior art approach also does not protect from leaking of malignant cells to the periphery. This idea will enable sealing of the tissue with staples at its ends to prevent such leakage. Optionally, it will be done with the help of a laparoscopic device that will serve as an anvil. Unlike the prior art procedure, the present invention will optionally use a balloon inflated in the lumen of the colon or any other resected organ before stapling, and by this assure the anastomosis will be ideal with the best possible approximation of the edges.

The use of colonoscopic techniques in the present invention provides another benefit not realized by a purely laparoscopic approach. Since colonoscopic examination is at present the most definitive diagnostic method for identifying diseases of the colon, locating the lesions through the exterior of the colon by laparoscopy or even by direct visualization can be somewhat problematic. Using the colonoscope to identify and isolate the diseased portion of the colon from within the lumen helps assure that the correct portions of the colon wall are excised and makes clean surgical margins without residual disease more assured as well.

In a preferred embodiment, the present invention utilizes a steerable colonoscope as described in U.S. patent application Ser. No. 09/790,204 (now U.S. Pat. No. 6,468,203); Ser. No. 09/969,927; and Ser. No. 10/229,577, which have been incorporated by reference. The steerable colonoscope described therein provides a number of additional benefits for performing endoscopic colectomy according to the present invention. The steerable colonoscope uses serpentine motion to facilitate rapid and safe insertion of the colonoscope into the patient's colon, which allows the endoscopic colectomy method to be performed more quickly and more safely. Beyond this however, the steerable colonoscope has the capability to create a three-dimensional mathematical model or map of the patient's colon and the location of any lesions identified during the initial examination. Lesions found during a previous examination by CT, MRI or any other imaging technology can also be mapped onto the three-dimensional mathematical model of the colon. By generating a three-dimensional map of the colon, the system knows where each part of the endoscope is in the colon and will be able to localize the two parts of the dissecting and stapling system exactly in the desired location. During surgery, this information can be used to quickly and accurately return the colonoscope to the location of the identified lesions where the colonoscope-mounted colectomy device will be used to complete the endoscopic colectomy procedure.

BRIEF DESCRIPTION OF THE DRAWINGS

FIGS. 13A-13B show exploded isometric assembly views of two adjacent segments and an individual segment, respectively, from the embodiment shown in FIG. 12.

FIGS. 15B to 15F show the use of three tendons to actuate a controllable segment used in the endoscope of the present invention.

FIGS. 16A and 16B show the use of two tendons to actuate a controllable segment in the endoscope of the present invention.

FIGS. 16C and 16D show the use of four tendons to actuate a controllable segment in the endoscope of the present invention.

FIGS. 18A and 18B show an end view and a side view, respectively, of a vertebra-type control ring which may be used to form the controllable segments of the endoscope of the present invention.

FIG. 18C shows a side view of interconnected vertebra-type control rings used to form the controllable segments of the endoscope of the present invention.

DETAILED DESCRIPTION OF THE INVENTION

Figure 2:
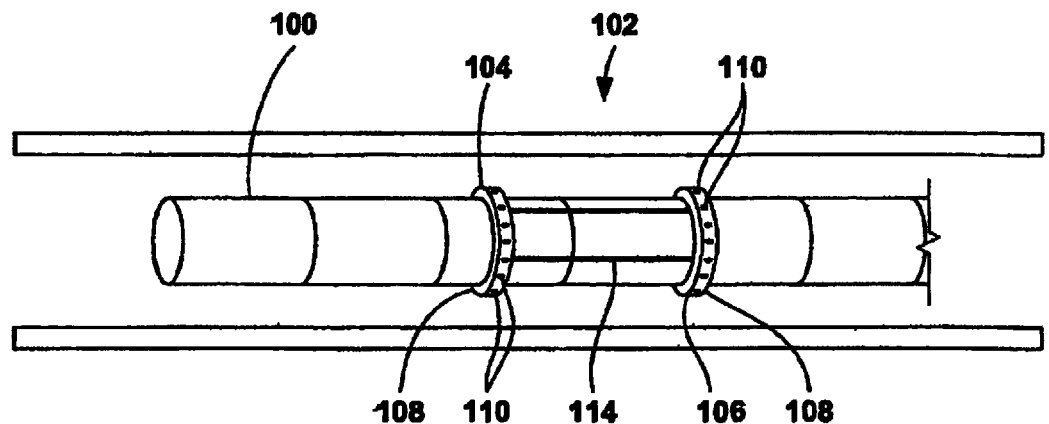
FIG. 2 is a cutaway drawing illustrating a steerable colonoscope with a colectomy device mounted thereon being inserted through the lumen of a patient's colon.

FIG. 2 is a cutaway drawing illustrating a steerable colonoscope 100 with a colectomy device 102 mounted thereon being inserted through the lumen of a patient's colon. As mentioned before, the same technique may apply for every other tubular shaped organ. Preferably, the steerable colonoscope 100 is constructed as described in U.S. patent application Ser. No. 09/790,204 (now U.S. Pat. No. 6,468,203); Ser. No. 09/969,927 (now U.S. Pat. No. 6,610,007); and Ser. No. 10/229,577 (now U.S. Pat. No. 6,858,005), with multiple articulating segments that are controlled to move with a serpentine motion that facilitates insertion and withdrawal of the colonoscope with a minimum of contact and stress applied to the colon walls. Additional details and various embodiments of the steerable colonscope 100 are described below with reference to FIGS. 6-22. In addition, the control system of the steerable colonoscope 100 has the capability to construct a three-dimensional mathematical model or map of the colon as it advances through lumen under control of the operator. The three-dimensional mathematical model of the colon and the location and nature of any lesions identified in the course of an initial colonoscopic examination can be stored and used in performance of the endoscopic colectomy procedure. In alternate embodiments, the colectomy device 102 of the present invention may be mounted on a colonoscope of a different design and construction.

The colectomy device 102 can be permanently or removably mounted on the steerable colonoscope 100. The colectomy device 102 has a distal component 104 and a proximal component 106. The distal component 104 and the proximal component 106 each have an expandable member 108 and a gripping mechanism 110 for gripping the wall of the colon. The expandable member 108 may be an inflatable balloon or a mechanically expandable mechanism. The gripping mechanism 110 may comprise a plurality of circumferentially located ports within which attachment points 112, e.g., needles, hooks, barbs, etc., may be retractably positioned about an exterior surface of the expandable member 108. Alternatively, the gripping mechanism 110 may utilize a vacuum gripper through a plurality of circumferentially located ports around the distal component 104 and/or the proximal component 106 or other known gripping mechanisms. In the case of the vacuum gripper, gripping mechanism 110 is in fluid communication through the ports and through the colonoscope 100 to the proximal end of the colonoscope 100 to a vacuum pump (not shown). At least one, and optionally both, of the distal component 104 and the proximal component 106 are movable longitudinally with respect to the body of the steerable colonoscope 100. Rails, grooves or the like 114 may be provided on the body of the steerable colonoscope 100 for guiding the longitudinal movement of the distal component 104 and the proximal component 106.

In addition, the colectomy device 102 includes a surgical stapler 116 or other anastomosis mechanism. The surgical stapler 116 is carried on either the distal component 104 or the proximal component 106 and a stapler anvil 118 is carried on the other of these components. The surgical stapler 116 may be configured similarly to any number of conventional stapling devices which are adapted to actuate staples into tissue. Another option is that there is a stapler and an anvil on both components for stapling and sealing the edges. Optionally, the colectomy device 102 may include a cutting device and/or electrocautery and/or a laser device for transecting the colon wall. Optionally, the colectomy device 102 may also include a vacuum mechanism or the like for drawing the excised tissue into the colectomy device 102 for later removal along with the steerable colonoscope 100.

FIG. 2 shows the steerable colonoscope 100 with the expandable members 108 of the distal component 104 and the proximal component 106 in a contracted or deflated condition for easy passage through the lumen of the patient's colon. The control system of the steerable colonoscope 100 monitors the position of each segment of the colonoscope 100 as it is advanced within the colon and can signal to the operator when the segments carrying the distal component 104 and the proximal component 106 of the colectomy device 102 are correctly positioned with respect to a previously detected lesion in the colon. Alternatively, the control system of the steerable colonoscope 100 can be programmed to advance the colonoscope 100 automatically through the lumen of the colon and to stop it when the distal component 104 and the proximal component 106 of the colectomy device 102 are correctly positioned with respect to the lesion in the colon. Alternatively, the control system will be able to automatically guide and deliver the two components to the desired location after the colonoscope has been inserted to the colon.

Figure 1:
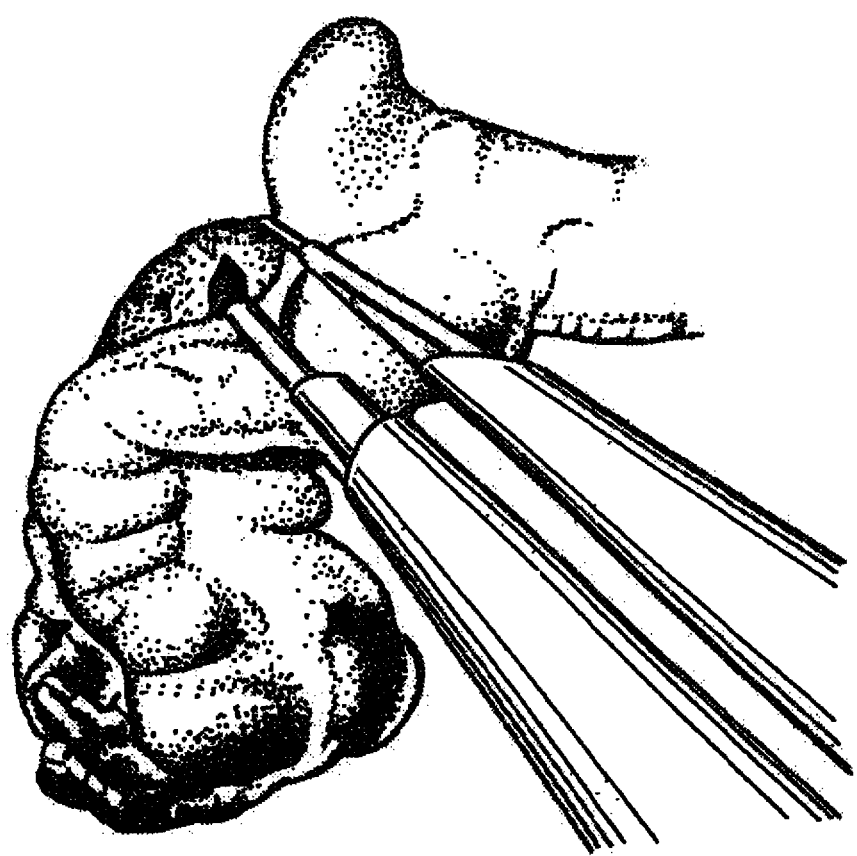
FIG. 1 is a phantom drawing illustrating a diseased portion of the colon being separated from the omentum using laparoscopic techniques through a small incision in a patient's abdomen.
Figure 3:
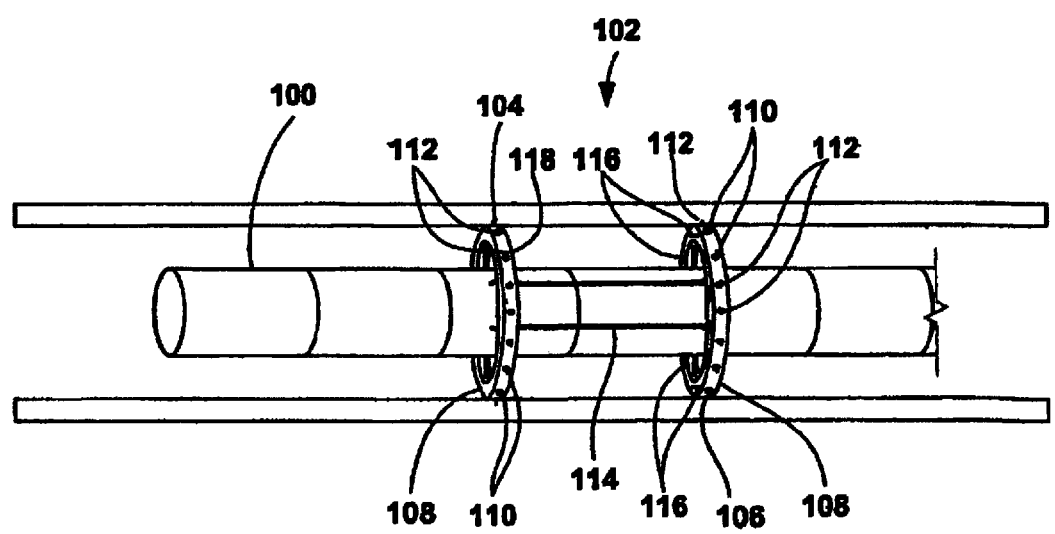
FIG. 3 is a cutaway drawing showing the gripping mechanism of the colonoscope-mounted colectomy device expanded within the lumen of the colon.

FIG. 3 is a cutaway drawing showing the expandable members 108 of the distal component 104 and the proximal component 106 of the colonoscope-mounted colectomy device 102 expanded within the lumen of the colon so that the gripping mechanism 110 grips the wall of the colon. The distal component 104 and the proximal component 106 may be expanded through any number of expansion devices. For instance, they may be radially expanded upon spoke-like support structures or they may be configured to radially expand in a rotational motion until the desired expansion diameter is attained. At this point, with the diseased portion of the colon identified and isolated by the colonoscope-mounted colectomy device 102, the diseased portion is separated from the omentum and the blood vessels supplying it are ligated and/or cauterized using laparoscopic techniques. FIG. 1 is a phantom drawing illustrating a diseased portion of the colon being separated from the omentum using laparoscopic techniques through a small incision in a patient's abdomen.

Figure 4:
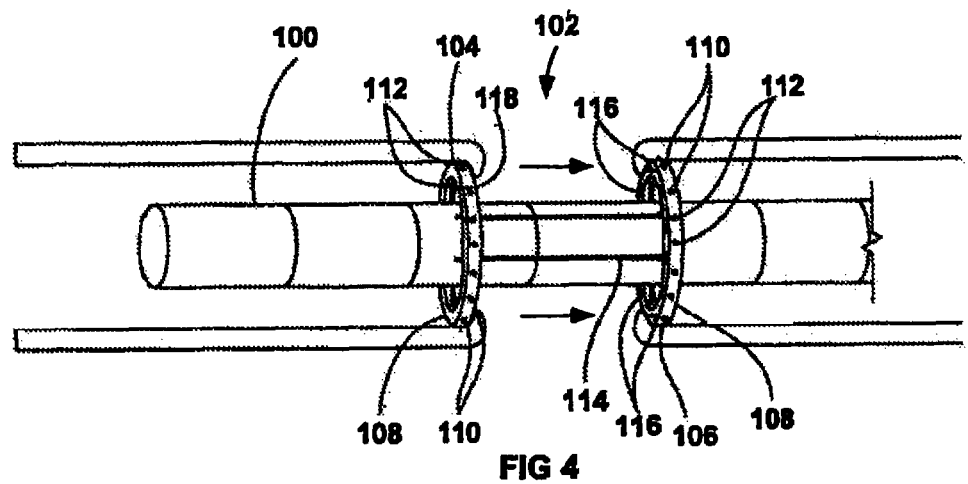
FIG. 4 illustrates the colon after the diseased portion has been excised and removed with the colonoscope-mounted colectomy device in position to approximate the transected ends of the colon.

Next, the diseased portion of the colon is excised by transecting the colon at the proximal and distal end of the diseased portion. The colon may be transected using laparoscopic techniques or using a cutting mechanism and/or electrocautery device mounted on the colectomy device 102. The excised tissue is removed using the laparoscope or drawn into the colectomy device 102 for later removal upon withdrawal of the steerable colonoscope 100. FIG. 4 illustrates the colon after the diseased portion has been excised and removed with the colonoscope-mounted colectomy device 102 in position to approximate the transected ends of the colon.

Figure 5:
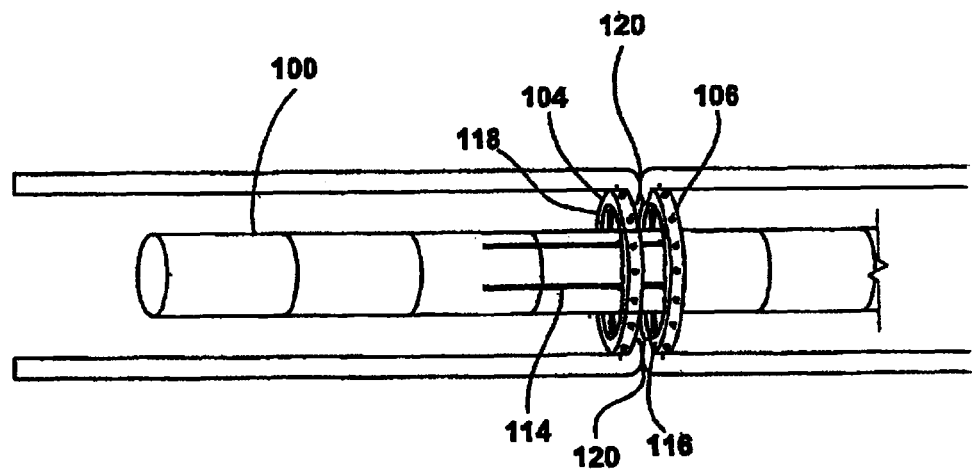
FIG. 5 illustrates the colonoscope-mounted colectomy device performing an end-to-end anastomosis to complete the endoscopic colectomy procedure.

The remaining ends of the colon are approximated one to the other by moving the distal component 104 and/or the proximal component 106 longitudinally with respect to the body of the steerable colonoscope 100, as shown by the arrows. Optionally, the proximal component 106 may be longitudinally translated towards the distal component 104 or both components 104, 106 may be approximated simultaneously towards one another. The ends of the colon are stapled to one another to create an end-to-end anastomosis 120 using the surgical stapler 116 and stapler anvil 118 on the colectomy device 102. Once the ends of the tissue have been approximated, staples or other fastening devices, e.g., clips, screws, adhesives, sutures, and combinations thereof, etc., may be actuated through the surgical stapler 116 such that they pierce both ends of the tissue against the stapler anvil 118. FIG. 5 illustrates the colonoscope-mounted colectomy device performing an end-to-end anastomosis 120 to complete the endoscopic colectomy procedure. Once the anastomosis 120 is complete, the expandable members 108 of the distal component 104 and the proximal component 106 are deflated or contracted and the steerable colonoscope 100 and the colectomy device 102 are withdrawn from the patient's body. The expanded members will assure a very accurate end-to-end anastomosis and prevent stenosis that can happen as a result of inaccurate approximation of the two ends.

In an alternative method using the colonoscope-mounted colectomy device 102, the diseased portion of the colon may be excised using a cutting device within the colectomy device 102 after the ends of the diseased portion have been approximated and anastomosed. The excised tissue is drawn into the colectomy device 102 and removed when the steerable colonoscope 100 is withdrawn from the patient.

In another alternative method, the colectomy procedure may be performed entirely from the endolumenal approach using the colonoscope-mounted colectomy device 102 without laparoscopic assistance. This method would be particularly advantageous for resection of small portions of the colon where it may not be necessary to mobilize an extended portion of the colon from the omentum to achieve successful approximation and anastomosis. The three-dimensional mapping capability of the steerable colonoscope 102 would be used to locate previously identified lesions without laparoscopic assistance.

Steerable Colonoscope

Figure 6:
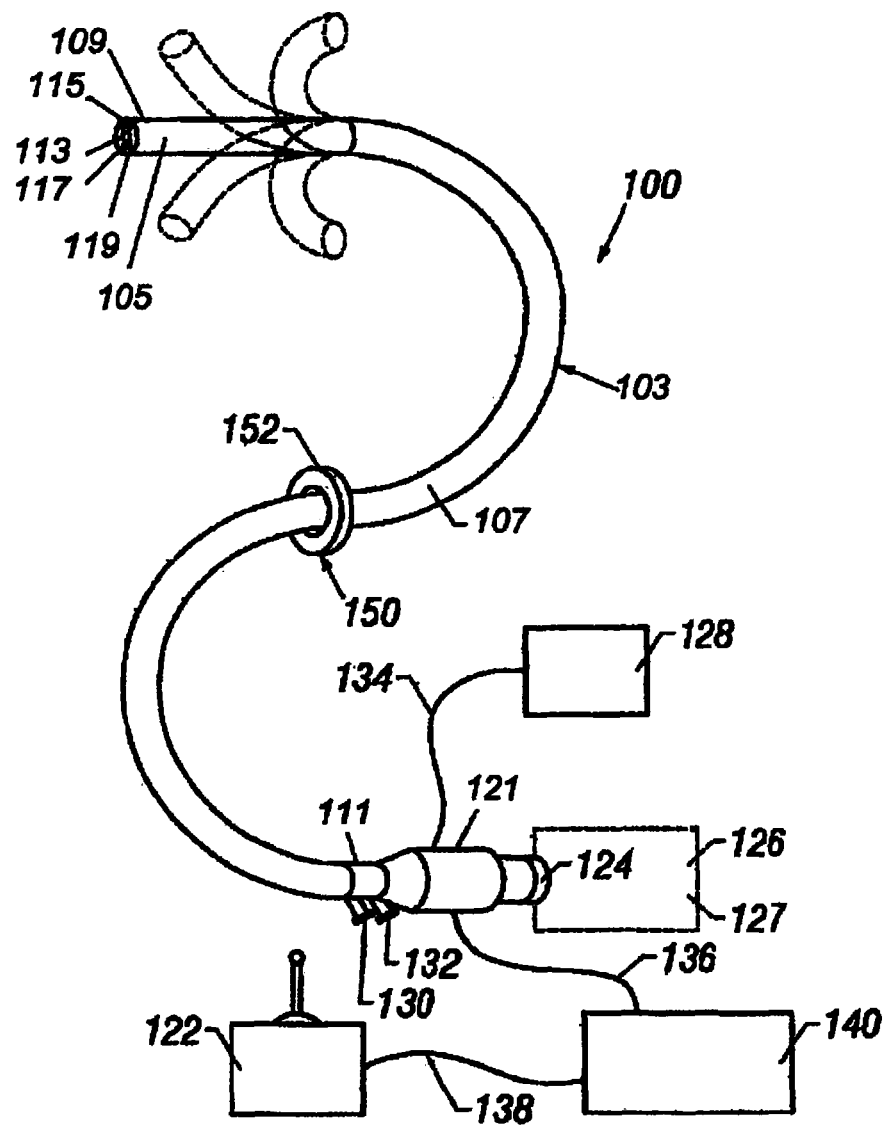
FIG. 6 shows a first embodiment of the steerable endoscope of the present invention.

FIG. 6 shows a first embodiment of the steerable endoscope 100 of the present invention. The endoscope 100 has an elongate body 103 with a manually or selectively steerable distal portion 105 and an automatically controlled proximal portion 107. The selectively steerable distal portion 105 can be selectively steered or bent up to a full 180 degree bend in any direction. A fiberoptic imaging bundle 113 and one or more illumination fibers 115 extend through the body 103 from the proximal end 111 to the distal end 109. Alternatively, the endoscope 100 can be configured as a video endoscope with a miniaturized video camera, such as a CCD camera, positioned at the distal end 109 of the endoscope body 103. The images from the video camera can be transmitted to a video monitor by a transmission cable or by wireless transmission. Optionally, the body 103 of the endoscope 100 may include one or two instrument channels 117, 119 that may also be used for insufflation or irrigation. The body 103 of the endoscope 100 is highly flexible so that it is able to bend around small diameter curves without buckling or kinking. When configured for use as a colonoscope, the body 103 of the endoscope 100 is typically from 135 to 185 cm in length and approximately 12-13 mm in diameter. The endoscope 100 can be made in a variety of other sizes and configurations for other medical and industrial applications.

A proximal handle 121 is attached to the proximal end 111 of the elongate body 103. The handle 121 includes an ocular 124 connected to the fiberoptic imaging bundle 113 for direct viewing and/or for connection to a video camera 126. The handle 121 is connected to an illumination source 128 by an illumination cable 134 that is connected to or continuous with the illumination fibers 115. A first luer lock fitting 130 and a second luer lock fitting 132 on the handle 121 are connected to the instrument channels 117, 119.

The handle 121 is connected to an electronic motion controller 140 by way of a controller cable 136. A steering control 122 is connected to the electronic motion controller 140 by way of a second cable 138. The steering control 122 allows the user to selectively steer or bend the selectively steerable distal portion 105 of the body 103 in the desired direction. The steering control 122 may be a joystick controller as shown, or other known steering control mechanism. The electronic motion controller 140 controls the motion of the automatically controlled proximal portion 107 of the body 103. The electronic motion controller 140 may be implemented using a motion control program running on a microcomputer or using an application-specific motion controller. Alternatively, the electronic motion controller 140 may be implemented using a neural network controller.

An axial motion transducer 150 is provided to measure the axial motion of the endoscope body 103 as it is advanced and withdrawn. The axial motion transducer 150 can be made in many possible configurations. By way of example, the axial motion transducer 150 in FIG. 6 is configured as a ring 152 that surrounds the body 103 of the endoscope 100. The axial motion transducer 150 is attached to a fixed point of reference, such as the surgical table or the insertion point for the endoscope 100 on the patient's body. As the body 103 of the endoscope 100 slides through the axial motion transducer 150, it produces a signal indicative of the axial position of the endoscope body 103 with respect to the fixed point of reference and sends a signal to the electronic motion controller 140 by telemetry or by a cable (not shown). The axial motion transducer 150 may use optical, electronic or mechanical means to measure the axial position of the endoscope body 103. Other possible configurations for the axial motion transducer 150 are described below.

Figure 7:
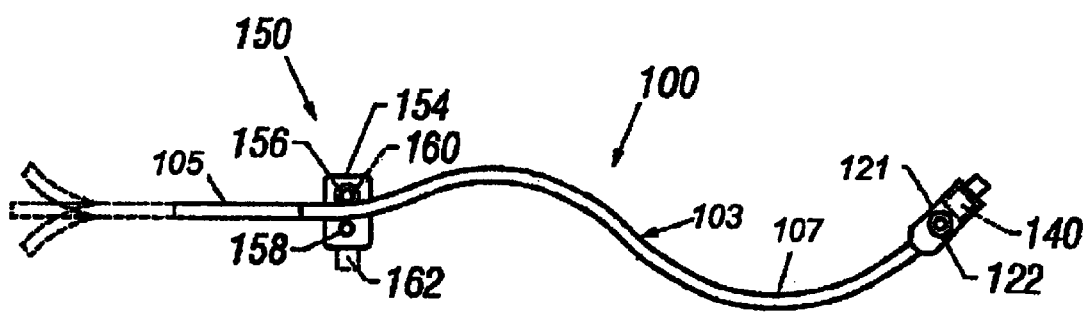
FIG. 7 shows a second embodiment of the steerable endoscope of the present invention.

FIG. 7 shows a second embodiment of the endoscope 100 of the present invention. As in the embodiment of FIG. 6, the endoscope 100 has an elongate body 103 with a selectively steerable distal portion 105 and an automatically controlled proximal portion 107. The steering control 122 is integrated into proximal handle 121 in the form or one or two dials for selectively steering the selectively steerable distal portion 105 of the endoscope 100. Optionally, the electronic motion controller 140 may be miniaturized and integrated into proximal handle 121, as well. In this embodiment, the axial motion transducer 150 is configured with a base 154 that is attachable to a fixed point of reference, such as the surgical table. A first roller 156 and a second roller 158 contact the exterior of the endoscope body 103. A multi-turn potentiometer 160 or other motion transducer is connected to the first roller 156 to measure the axial motion of the endoscope body 103 and to produce a signal indicative of the axial position.

The endoscope 100 may be manually advanced or withdrawn by the user by grasping the body 103 distal to the axial motion transducer 150. Alternatively, the first roller 156 and/or second roller 158 may be connected to a motor 162 for automatically advancing and withdrawing the body 103 of the endoscope 100.

Figure 8:
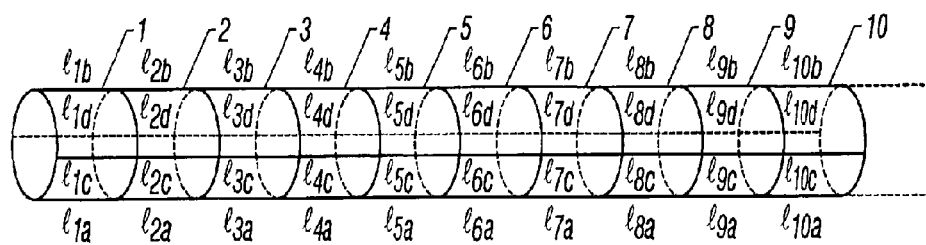
FIG. 8 shows a wire frame model of a section of the body of the endoscope in a neutral or straight position.

FIG. 8 shows a wire frame model of a section of the body 103 of the endoscope 100 in a neutral or straight position. Most of the internal structure of the endoscope body 103 has been eliminated in this drawing for the sake of clarity. The endoscope body 103 is divided up into sections 1, 2, 3 . . . 10, etc. The geometry of each section is defined by four length measurements along the a, b, c and d axes. For example, the geometry of section 1 is defined by the four length measurements $l_{1a}, l_{1b}, l_{1c}, l_{1d}$, and the geometry of section 2 is defined by the four length measurements $l_{2a}, l_{2b}, l_{2c}, l_{2d}$, etc. Preferably, each of the length measurements is individually controlled by a linear actuator (not shown). The linear actuators may utilize one of several different operating principles. For example, each of the linear actuators may be a self-heating NiTi alloy linear actuator or an electrorheological plastic actuator, or other known mechanical, pneumatic, hydraulic or electromechanical actuator. The geometry of each section may be altered using the linear actuators to change the four length measurements along the a, b, c and d axes. Preferably, the length measurements are changed in complementary pairs to selectively bend the endoscope body 103 in a desired direction. For example, to bend the endoscope body 103 in the direction of the a axis, the measurements $l_{1a}, l_{2a}, l_{3a} \ldots l_{10a}$, would be shortened and the measurements $l_{1b}, l_{2b}, l_{2b} \ldots l_{10b}$, would be lengthened an equal amount. The amount by which these measurements are changed determines the radius of the resultant curve.

In the selectively steerable distal portion 105 of the endoscope body 103, the linear actuators that control the a, b, c and d axis measurements of each section are selectively controlled by the user through the steering control 122. Thus, by appropriate control of the a, b, c and d axis measurements, the selectively steerable distal portion 105 of the endoscope body 103 can be selectively steered or bent up to a full 180° in any direction.

Figure 9:
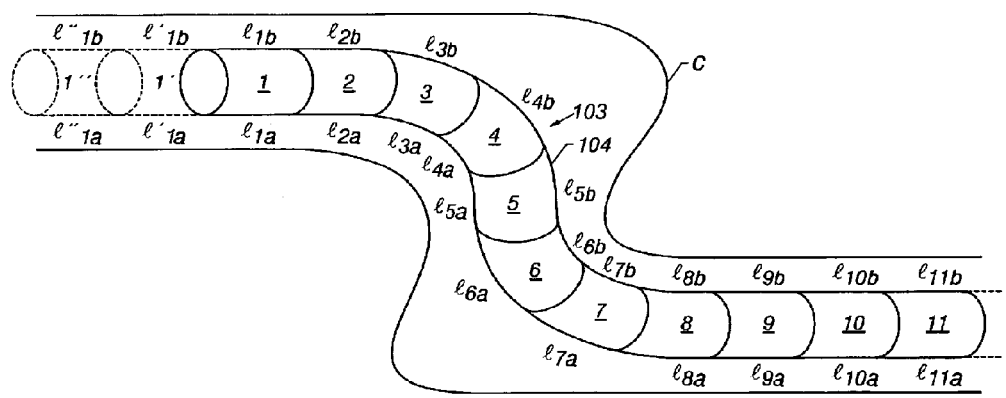
FIG. 9 shows the wire frame model of the endoscope body shown in FIG. 8 passing through a curve in a patient's colon.

In the automatically controlled proximal portion 107, however, the a, b, c and d axis measurements of each section are automatically controlled by the electronic motion controller 140, which uses a curve propagation method to control the shape of the endoscope body 103. To explain how the curve propagation method operates, FIG. 9 shows the wire frame model of a part of the automatically controlled proximal portion 107 of the endoscope body 103 shown in FIG. 8 passing through a curve in a patient's colon C. For simplicity, an example of a two-dimensional curve is shown and only the a and b axes will be considered. In a three-dimensional curve all four of the a, b, c and d axes would be brought into play.

In FIG. 9, the endoscope body 103 has been maneuvered through the curve in the colon C with the benefit of the selectively steerable distal portion 105 (this part of the procedure is explained in more detail below) and now the automatically controlled proximal portion 107 resides in the curve. Sections 1 and 2 are in a relatively straight part of the colon C, therefore $l_{1a} = l_{1b}$, and $l_{2a} = l_{2b}$. However, because sections 3-7 are in the S-shaped curved section, $l_{3a} < l_{3b}, l_{4a} < l_{4b}$, and $l_{5a} < l_{5b}$, but $l_{6a} > l_{6b}, l_{7a} > l_{7ab}$ and $l_{8a} > l_{8ab}$. When the endoscope body 103 is advanced distally by one unit, section 1 moves into the position marked 1', section 2 moves into the position previously occupied by section 1, section 3 moves into the position previously occupied by section 2, etc. The axial motion transducer 150 produces a signal indicative of the axial position of the endoscope body 103 with respect to a fixed point of reference and sends the signal to the electronic motion controller 140. Under control of the electronic motion controller 140, each time the endoscope body 103 advances one unit, each section in the automatically controlled proximal portion 106 is signaled to assume the shape of the section that previously occupied the space that it is now in. Therefore, when the endoscope body 103 is advanced to the position marked 1', $l_{1a} = l_{1ab}, l_{2a} = l_{2b}, l_{3a} = l_{3b}, l_{4a} < l_{4b}, l_{5a} < l_{5b}, l_{6a} << l_{6b}, l_{7a} > l_{7b}, l_{8a} > l_{8b}$, and $l_{9a} > l_{9b}$, and, when the endoscope body 103 is advanced to the position marked 1", $l_{1a} = l_{1b}, l_{2a} = l_{2b}, l_{3a} = l_{3b}, l_{4a} = l_{4b}, l_{5a} < l_{5b}, l_{6a} < l_{6b}, l_{7a} < l_{7b}, l_{8a} > l_{8b}, l_{9a} > l_{9b}$, and $l_{10a} > l_{10b}$. Thus, the S-shaped curve propagates proximally along the length of the automatically controlled proximal portion 107 of the endoscope body 103. The S-shaped curve appears to be fixed in space, as the endoscope body 103 advances distally.

Similarly, when the endoscope body 103 is withdrawn proximally, each time the endoscope body 103 is moved proximally by one unit, each section in the automatically controlled proximal portion 107 is signaled to assume the shape of the section that previously occupied the space that it is now in. The S-shaped curve propagates distally along the length of the automatically controlled proximal portion 107 of the endoscope body 103, and the S-shaped curve appears to be fixed in space, as the endoscope body 103 withdraws proximally.

Whenever the endoscope body 103 is advanced or withdrawn, the axial motion transducer 150 detects the change in position and the electronic motion controller 144) propagates the selected curves proximally or distally along the automatically controlled proximal portion 107 of the endoscope body 103 to maintain the curves in a spatially fixed position. This allows the endoscope body 103 to move through tortuous curves without putting unnecessary force on the wall of the colon C.

Figure 10:
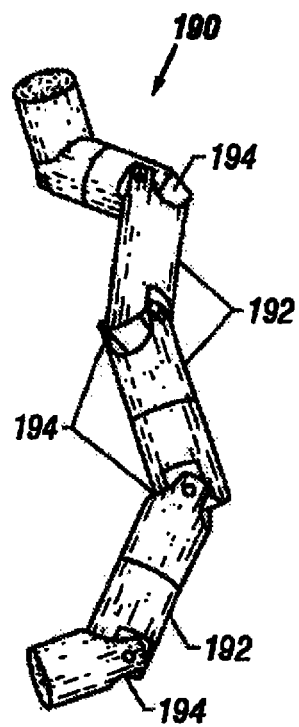
FIG. 10 shows a representative portion of an alternative endoscopic body embodiment having multiple segments interconnected by joints.
Figure 11:
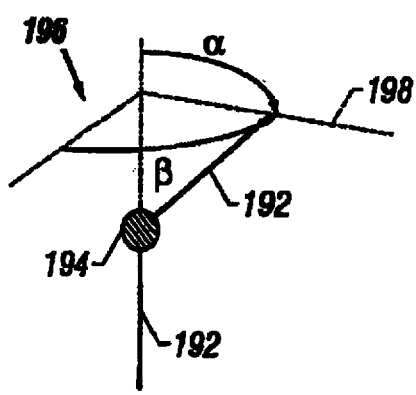
FIG. 11 shows a partial schematic representation of the embodiment of FIG. 10 showing two segments being pivotable about two independent axes.

FIG. 10 shows a representative portion of an alternative endoscopic body embodiment 190 which has multiple segments 192 interconnected by joints 194. In this embodiment, adjacent segments 192 can be moved or angled relative to one another by a joint 194 having at least one degree-of-freedom, and preferably having multiple degrees-of-freedom, preferably about two axes as shown here. As seen further in FIG. 4, a partial schematic representation 196 of the embodiment 190 is shown where two segments 192 may be rotated about joint 194 about the two independent axes. The range of motion may be described in relation to spherical axes 198 by angles α and β

Figure 12:
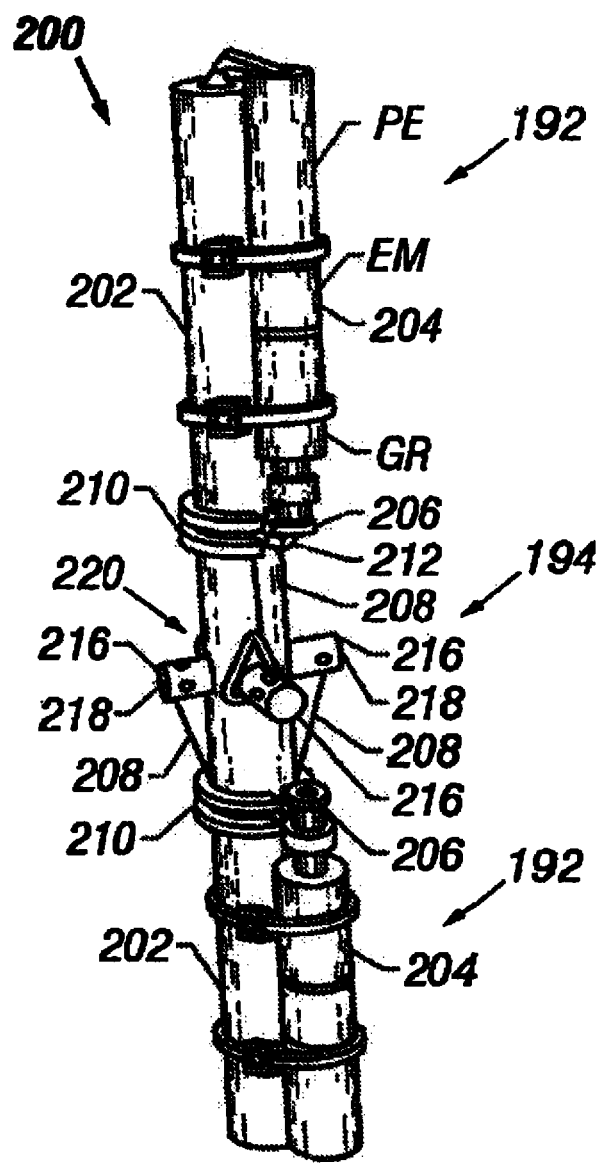
FIG. 12 shows a preferable endoscope embodiment having motorized segmented joints.

As mentioned above, such a segmented body may be actuated by a variety of methods. A preferable method involves the use of electromechanical motors individually mounted on each individual segment to move the segments relative to one another. FIG. 12 shows a preferable embodiment 200 having motorized segmented joints. Each segment 192 is preferably comprised of a backbone segment 202, which also preferably defines at least one lumen running through it to provide an access channel through which wires, optical fibers, air and/or water channels, various endoscopic tools, or any variety of devices and wires may be routed through. The backbone segment may be made of a variety of materials which are preferably biocompatible and which provide sufficient strength to support the various tools and other components, e.g., stainless steel. Although much of the description is to an individual segment 192, each of the segments 192 are preferably identical, except for the segment (or first few segments) located at the distal tip, and the following description readily applies to at least a majority of the segments 192.

A single motor, or multiple motors depending upon the desired result and application, may be attached to at least a majority of the segments. An embodiment having a single motor on a segment is illustrated in FIG. 12 where an individual motor 204 is preferably attached to backbone 202 and is sufficiently small and compact enough so as to present a relatively small diameter which is comfortable and small enough for insertion into a patient without trauma. Motor 204, which is shown here as being a small brushed DC motor, may be used for actuating adjacent segments 192 and may be controlled independently from other motors. Various motors, aside from small brushed DC motors, may also be used such as AC motors, linear motors, etc. Each motor 204 also preferably contains within the housing not only the electromechanical motor assembly EM itself, but also a gear reduction stage GR, and a position encoder PE. A gear reduction stage GR attached to the motor assembly EM will allow for the use of the motor 204 in its optimal speed and torque range by changing high-speed, low-torque operating conditions into a more useful low-speed, high-torque output. The position encoder PE may be a conventional encoder to allow the controlling computer to read the position of the segment's joint 194 by keeping track of the angular rotational movement of the output shaft of the motor 204.

Each motor 204 has a rotatable shaft which extends from an end of the motor 204 to provide for the transmission of power to actuate the segments 192. Upon this shaft, a spool 206 may be rotatingly attached with a first end of the cable 208 further wound about the spool 206. The cable 208 may then be routed from spool 206 through a channel 212 which is defined in the cable guide 210 and out through opening 214 (as seen in greater detail in FIGS. 13A-13B) to cable anchor 216, to which the second end of the cable 208 is preferably attached, e.g., by crimping and/or soldering. The cable guide 210 serves to capture the cable 208 that is wound about the spool 206. The cable anchor 216 is attached across a universal joint pivot 220 to an adjacent segment 192 via a pin 218 and may be shaped like a conventional electronic ring connector having a round section defining a hole therethrough for mounting to the segment 192 and an extension protruding from the anchor 216 for attaching the second end of the cable 208. Cable 208 may comprise a wide variety of filaments, strands, wires, chains, braids, etc. any of which may be made of a wide variety of biocompatible materials, e.g., metals such as stainless steel, polymers such as plastics and Nylon, etc.

In operation, when the motor 204 is operated to spin the shaft in a first direction, e.g., clockwise, the spool 206 rotates accordingly and the cable 208 pulls in a corresponding direction on the adjacent segment 192 and transmits the torque to subsequently actuate it along a first axis. When the motor 204 is operated to spin the shaft in a second direction opposite to the first, e.g., counter-clockwise, the spool 206 again rotates accordingly and the cable 208 would then pull in the corresponding opposing direction on the adjacent segment 192 to subsequently transmit the torque and actuate it in the opposite direction.

FIGS. 13A and 13B show exploded isometric assembly views of two adjacent segments and an individual segment, respectively, from the embodiment shown in FIG. 12. As seen in FIG. 13A, backbone 202 is seen with the lumen 221, which may be used to provide a working channel, as described above. Also seen are channel 212 defined in cable guide 210 as well as opening 214 for the cable 208 to run through. In interconnecting adjacent segments and to provide the requisite degree-of-freedom between segments, a preferable method of joining involves using the universal joint pivot 220. However, other embodiments, rather than using a universal joint pivot 220, may use a variety of joining methods, e.g., a flexible tube used to join two segments at their respective centers, a series of single degree-of-freedom joints that may be closely spaced, etc. This particular embodiment describes the use of the universal joint pivot 220. At the ends of backbone 202 adjacent to other segments, a pair of universal yoke members 224 may be formed with a pair of corresponding pin openings 226. As the universal joint pivot 220 is connected to a first pair of yoke members 224 on one segment, a corresponding pair of yoke members 224 from the adjacent segment may also be attached to the joint pivot 220.

As seen further in FIG. 13B, the universal joint pivot 220 is shown in this embodiment as a cylindrical ring having two sets of opposing receiving holes 228 for pivotally receiving corresponding yoke members 224. The receiving holes 228 are shown as being spaced apart at 90.degree. intervals, however, in other variations, receiving holes may be spaced apart at other angles depending upon the desired degree-of-freedom and application. Also seen is an exploded assembly of spool 206 removed from motor 204 exposing drive shaft 205. With motor 204 displaced from backbone 202, the groove 230 is revealed as formed in the backbone 202. This groove 230 may be depressed in backbone 202 to preferably match the radius of the motor 204 housing not only to help locate the motor 204 adjacent to backbone 202, but also to help in reducing the overall diameter of the assembled segment. The motor 204 may be attached to the backbone 202 by various methods, e.g., adhesives, clamps, bands, mechanical fasteners, etc. A notched portion 232 may also be formed in the cable guide 210 as shown to help in further reducing segment diameter.

Prior to insertion into a patient, the endoscope 200 may optionally be configured to have a diagnostic check performed automatically. When the endoscope 200 is wound onto a drum, adjacent segments 192 will have a predetermined angle relative to one another, as determined initially by the diameter of the drum and the initial configuration of the storage unit in which the endoscope 200 may be positioned. During a diagnostic check before insertion, a computer may be configured to automatically sense or measure the angles between each adjacent segments 192. If any of the adjacent segments 192 indicate a relative measured angle out of a predetermined acceptable range of angles, this may indicate a segment 192 being out of position and may indicate a potential point of problems during endoscope 200 use. Accordingly, the computer may subsequently sound an audible or visual alarm and may also place each of the segments 192 into a neutral position to automatically prevent further use or to prevent any trauma to the patient.

Figure 14:
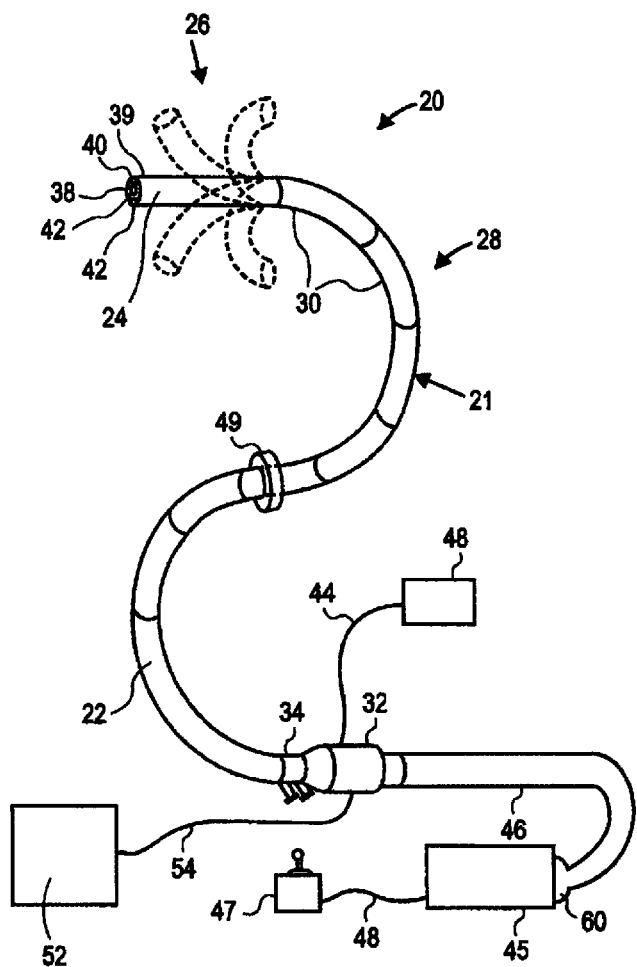
FIG. 14 shows a variation of the tendon driven endoscope of the present invention.

FIG. 14 shows a variation of the tendon driven endoscope 20 of the present invention. The endoscope 20 has an elongate body 21 with a manually or selectively steerable distal portion 24, an automatically controlled portion 28, and a flexible and passively manipulated proximal portion 22, which may be optionally omitted from the device. The steerable distal portion 24 can be articulated by hand or with mechanical assistance from actuators. The automatically controlled portion 28 is segmented, and each segment is capable of bending through a full range of steerable motion. The distal portion 24 is also a controllable segment.

The selectively steerable distal portion 24 can be selectively steered or bent up to, e.g., a full 180.degree. bend in any direction 26, as shown. A fiberoptic imaging bundle 40 and one or more illumination fibers 42 may extend through the body 21 from the proximal portion 22 to the distal portion 24. Alternatively, the endoscope 20 may be configured as a video endoscope with a miniaturized video camera, such as a CCD or CMOS camera, positioned at the distal portion 24 of the endoscope body 21. The images from the video camera can be transmitted to a video monitor by a transmission cable or by wireless transmission where images may be viewed in real-time and/or recorded by a recording device onto analog recording medium, e.g., magnetic tape, or digital recording medium, e.g., compact disc, digital tape, etc. LEDs or other light sources could also be used for illumination at the distal tip of the endoscope.

The body 21 of the endoscope 20 may also include one or more access lumens 38 that may optionally be used for illumination fibers for providing a light source, insufflation or irrigation, air and water channels, and vacuum channels. Generally, the body 21 of the endoscope 20 is highly flexible so that it is able to bend around small diameter curves without buckling or kinking while maintaining the various channels intact. When configured for use as a colonoscope, the body 21 of the endoscope 20 may range typically from 135 to 185 cm in length and about 13-19 mm in diameter. The endoscope 20 can be made in a variety of other sizes and configurations for other medical and industrial applications.

The controllable portion 28 is composed of at least one segment 30, and preferably several segments 30, which are controllable via a computer and/or electronic controller (controller) 45 located at a distance from the endoscope 20. Each of the segments 30 has tendons mechanically connected to actuators to allow for the controlled motion of the segments 30 in space. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, heat, etc., to each of the bundles to actuate a linear motion in the wire bundles which in turn actuate the tendon movement. The linear translation of the actuators within the controller may be configured to move over a relatively short distance, e.g., within a few inches or less such as .+-0.1 inch, to accomplish effective articulation depending upon the desired degree of segment movement and articulation.

It is preferable that the length of the insertable portion of the endoscope comprises controllable segments 30, although a passive proximal portion 22 can also be used. This proximal portion 22 is preferably a flexible tubing member that may conform to an infinite variety of shapes, and may be made from a variety of materials such as thermoset and thermoplastic polymers which are used for fabricating the tubing of conventional endoscopes.

Each segment 30 preferably defines at least one lumen running throughout to provide an access channel through which wires, optical fibers, air and/or water channels, various endoscopic tools, or any variety of devices and wires may be routed. A polymeric covering, or sheath, 39 may also extend over the body of the endoscope 21 including the controllable portion 28 and steerable distal portion 24. This sheath 39 can preferably provide a smooth transition between the controllable segments 30, the steerable distal portion 24, and the flexible tubing of proximal portion 22.

A handle 32 may be attached to the proximal end of the endoscope. The handle 32 may include an ocular connected to the fiberoptic imaging bundle 42 for direct viewing. The handle 32 may otherwise have a connector 54 for connection to a video monitor, camera, e.g., a CCD or CMOS camera, or a recording device 52. The handle 32 may be connected to an illumination source 43 by an illumination cable 44 that is connected to or continuous with the illumination fibers 42. Alternatively, some or all of these connections could be made at the controller 45. Luer lock fittings 34 may be located on the handle 32 and connected to the various instrument channels.

The handle 32 may be connected to a motion controller 45 by way of a controller cable 46. A steering controller 47 may be connected to the motion controller 45 by way of a second cable 48 or it may optionally be connected directly to the handle 32. Alternatively, the handle may have the steering control mechanism integrated directly into the handle, e.g., in the form of a joystick, conventional disk controllers such as dials, pulleys or wheels, etc. The steering controller 47 allows the user to selectively steer or bend the selectively steerable distal portion 24 of the body 21 in the desired direction 26. The steering controller 47 may be a joystick controller as shown, or other steering control mechanism, e.g., dual dials or rotary knobs as in conventional endoscopes, track balls, touchpads, mouse, or sensory gloves. The motion controller 45 controls the movement of the segmented automatically controlled proximal portion 28 of the body 21. This controller 45 may be implemented using a motion control program running on a microcomputer or using an application-specific motion controller. Alternatively, the controller 45 may be implemented using, e.g., a neural network controller.

The actuators applying force to the tendons may be included in the motion controller unit 45, as shown, or may be located separately and connected by a control cable. The tendons controlling the steerable distal portion 24 and the controllable segments 30 extend down the length of the endoscope body 21 and connect to the actuators. FIG. 14 shows a variation in which the tendons pass through the handle 32 and connect directly to the motion controller 45 via a quick-release connector 60. In this variation, the tendons are part of the control cable 46, although they could independently connect to the actuators, so long as the actuators are in communication with the controller 45.

An axial motion transducer (also called a depth referencing device or datum) 49 may be provided for measuring the axial motion, i.e., the depth change, of the endoscope body 21 as it is advanced and withdrawn. The depth referencing device 49 can be made in many possible configurations. For example, the axial motion transducer 49 in FIG. 14 is configured as a ring 49 that may surround the body 21 of the endoscope 20. The axial motion transducer 49 is preferably attached to a fixed point of reference, such as the surgical table or the insertion point for the endoscope 20 on the patient's body. As the body 21 of the endoscope 20 slides through the axial motion transducer 49, it indicates the axial position of the endoscope body 21 with respect to the fixed point of reference and sends a signal to the electronic controller 45 by telemetry or by a cable. The axial motion transducer 49 may use optical, electronic, magnetic, radio frequency or mechanical methods to measure the axial position of the endoscope body 21.

When the endoscope body 21 is advanced or withdrawn, the axial motion transducer 49 detects the change in position and signals the motion controller 45. The controller can use this information to propagate the selected curves proximally or distally along the controllable portion 28 of the endoscope body 21 to keep the endoscope actively following the pathway selected by the user steering the distal portion 24. The axial motion transducer 49 also allows for the incrementing of a current depth within the colon C by the measured change in depth. This allows the endoscope body 21 to be guided through tortuous curves without putting unnecessary force on the wall of the colon C.

Figure 15A:
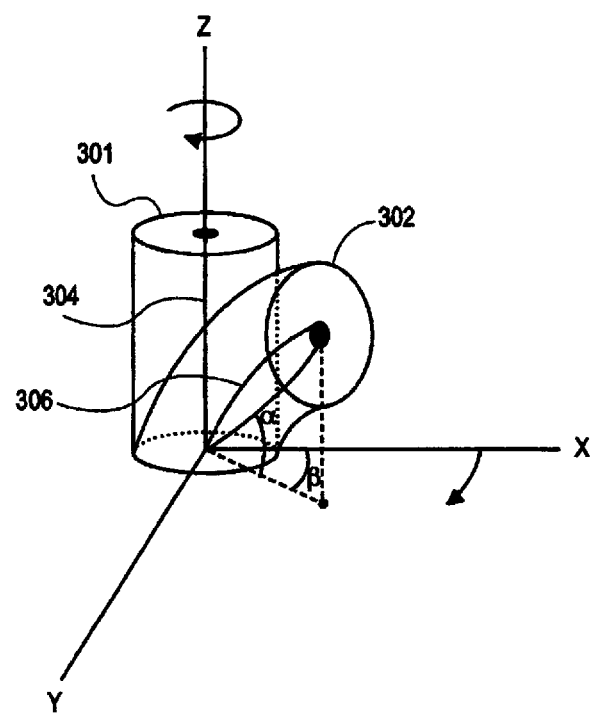
FIG. 15A shows the range of motion of a controllable segment of the present invention actuated by three tendons.

FIG. 15A shows an example of the resulting segment articulation which may be possible through the use of two or three tendons to articulate the controllable segments, including the steerable distal section. FIG. 15A shows one example of a possible range of motion of a controllable segment of the present invention actuated, in this example, by three tendons. A segment in the relaxed, upright position 301 can be bent in virtually any direction relative to the x-y plane. The figure, as an illustrative example, shows a segment 302 that has been bent down and at an angle relative to its original position 301. The angles α and β describe the bend assumed by the segment. Angle β gives the angle in the x-y plane, while a is the angle describing the motion in the x-z plane. In one variation, the controllable segments of the endoscope can bend through all 360° in the β angle and up to 90° in the α angle. An angle a greater than 90° would result in looping of the endoscope. In FIG. 15A, the segment is shown bent approximately 45° along angle α. The freedom of movement of a segment is, in part, determined by the articulation method, the size of the segment, the materials from which it is constructed, and the manner in which it is constructed, among others. Some of these factors are discussed herein.

The steerable distal portion, as well as the endoscope and the controllable segments are bendable but preferably not compressible or expansible. Thus, in FIG. 15A, the centerline 304 of the relaxed segment 301 is approximately the same length as the centerline 306 of the segment after bending 302.

FIGS. 15B to 15F show the use of three tendons to actuate a controllable segment used in an endoscope of the present invention. The tendons shown in this example are all Bowden type cables 310 that have an internal cable 312 coaxially surrounded by a housing or sleeve 314 in which the cable is free to move. Bowden cables can be used to apply either tensile or compressive forces, i.e., they may be pushed or pulled, to articulate the endoscope and can be actuated remotely to deliver forces as desired at locations along the endoscope. Force from a tendon is exerted across or through the segment by attaching the tendon cable at the distal end of the segment 320 and the tendon housing 314 at the proximal end of the segment 322. FIG. 15B shows a view of the top of the segment with three attachment sites for the tendon cables indicated 320.

In one variation, three tendons are used to actuate each segment, including the steerable distal portion, although four or more tendons could be used. Three tendons can reliably articulate a segment in any direction without having to rotate the segment or endoscope about its longitudinal axis. The three cable tendons 312 are preferably attached at the distal end of the segment 320 close to the segment's edge, spaced equally apart. In FIG. 15B, tendons are attached at the two o'clock, six o'clock and 10 o'clock positions. It is desirable to use fewer tendons, because of space concerns, since the tendons controlling each segment project proximally to the actuators. Thus, two tendons could be used to control a segment. It may also be desirable to include one or more biasing element, e.g., a spring, to assist in articulating a segment in three dimensions. In another variation, two tendons may be used to articulate a segment in three dimensional space by controlling motion in two directions while rotating the segment about its longitudinal axis.

FIG. 15C shows a relaxed segment with three tendons attached. The tendon sleeves 314 are shown attached to the proximal end of the segment 322 directly below the corresponding cable attachment sites. FIGS. 15D to 15F show this segment bent by each of the controlling tendons 310 separately.

As shown in FIG. 15D, applying tension by pulling on the first tendon 330 results in a bending in the direction of the first tendon 330. That is, looking down on the top of the unbent segment (as in FIG. 15B), if the first tendon is attached at the six o'clock position, then pilling on just this tendon results in bending the segment towards the six o'clock position. Likewise, in FIG. 15E, putting tension only on a second tendon 332 attached at the two o'clock position results in bending the segment towards the two o'clock direction. Finally, pulling on the tendon in the ten o'clock position 334 bends the segment towards the ten o'clock direction. In all cases, the bending is continuous; the greater the tension applied, the further the bending (the α angle, in the x-z plane of FIG. 15A). A segment can be bent in any direction by pulling on individual tendons or a combination of two tendons. Thus, to bend the segment in the twelve o'clock direction, both the second 332 and the third 334 tendon could be pulled with equal force. Alternatively, first tendon 330 in the six o'clock position may be pushed either alone or in combination with second 332 and third tendons 334 being pulled to result in the same configuration.

FIGS. 16A and 16B show a variation in which a segment is articulated by two tendons and one biasing element. FIG. 16A shows a planar top view of the segment. The attachment sites for the biasing element 340 and the two tendons 320 are spaced around the perimeter of the distal end of the segment as shown. The tendons 320 may be attached at the two o'clock and ten o'clock positions, looking down on the top of the section, and the biasing element 340 is attached at the six o'clock position. FIG. 16B shows a perspective view of the segment in the unbent configuration. In this variation, the biasing element is configured to apply tension to the side of the segment such that it will bend towards the six o'clock position. The biasing element can be any element that can apply compressive or tensile forces across the segment, e.g. a spring, elastic element, a piston, etc. The segment is held in the neutral or unbent position shown in FIG. 16B by applying tension from both tendons 312. Controlling the amount of tension applied by the tendons results in bending of the segment in three dimensional space. More than one biasing element could also be used with two or more tendons. For example, a biasing element could be located opposite each tendon.

Alternatively, if the tendon is a push-pull cable, and each tendon can apply compression as well as tension, then two tendons can control the motion of segment without any biasing element at all.

More than three tendons can also be used to control the bending of a segment. FIG. 16C shows a top planar view of a segment that is controlled by four tendons attached in the eleven o'clock, two o'clock, five o'clock and eight o'clock positions. As with the three-tendon embodiment, tension applied on one or a combination of the tendons results in shortening the side of the segment. Thus, if tension is applied only on the tendon attached distally at the eleven o'clock position 355, the corresponding side of the tendon will shorten, and the segment will bend in the eleven o'clock direction.

In all these variations, the circumferential locations of the tendons and/or biasing elements are illustrative and are not intended to be limited to the examples described herein. Rather, they may be varied according to the desired effects as understood by one of skill in the art.

Figure 17:
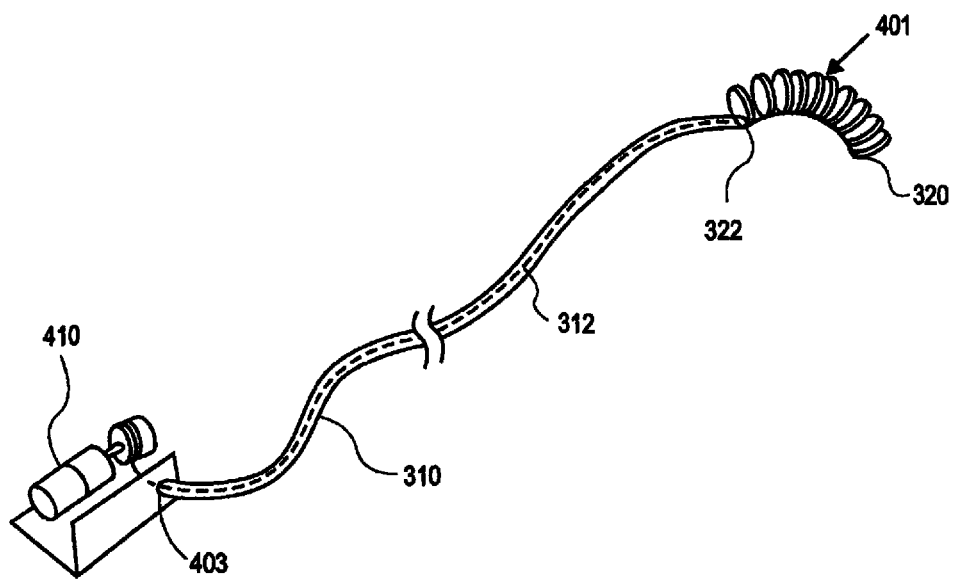
FIG. 17 shows a partial schematic representation of a single tendon bending a segment.

FIG. 17 shows a partial schematic representation of a single tendon bending a segment. For clarity, the other parts of a complete endoscope, including other tendons and segments, have been omitted from FIG. 17. Tension applied to a tendon cable is transferred across the entire segment, resulting in bending. By using a Bowden cable 310 whose sleeve 314 is attached to the base 322 of the segment and also fixed at the proximal actuator end 403, only the intended segment 401 is bent by applying tension to the tendon 312, and more proximal segments are unaffected. The tendon is placed in tension by the actuator 410, which is shown, in this variation, as a motor pulling on the tendon cable 312.

Linked control rings may provide the flexible structure needed to construct the steerable distal portion and the controllable segments. Two examples of the types of control rings that may be utilized are shown. The first is shown in FIG. 18A which shows a vertebra-type control ring that forms the controllable segments of the present invention. FIG. 18A shows an end view of a single vertebra. Each ring-shaped vertebra 501 can define a central channel or aperture 504 or apertures that can collectively form the internal lumen of the device as previously described. The vertebrae may have two pairs of hinges; the first pair 506 projecting perpendicularly from a first face of the vertebra and a second pair 508, located 90° around the circumference from the first pair, projecting perpendicularly away from the face of the vertebra on a second face of the vertebra opposite to the first face. The hinges shown in FIGS. 18A and 18B are tab-shaped, however other shapes may also be used.

The vertebra control ring in FIG. 18A is shown with three holes 510 through the edge of the vertebra that may act, e.g., as attachment sites for the tendon cable 312 if the vertebra is the most distal vertebra in a segment, or as a throughway for a tendon cable that can actuate the segment in which the vertebra is used. These holes 510 can also be used to attach the sleeve of the Bowden-type tendon cable 314 when the vertebra is the most proximal control disk in a segment. Alternatively, rather than a hole 510, the attachment sites could be a recess or other specialized shape. Although FIG. 18A shows three holes 510, the number of holes may depend upon the number of tendons used to control the segment to which the vertebra belongs. Since the holes 510 may be used as attachment sites for the tendons, there are as many holes as there are tendons controlling the segment.

The outer edge of the vertebra in FIG. 18A may be scalloped to provide spaces 512 for tendon housings of tendons that control more distal segments and bypass the vertebra. These tendon bypass spaces preferably conform to the outer diameter of the tendons used. The number of tendon bypass spaces 512 may vary depending on the number of tendons. Also, the orientation of the tendon bypass spaces may be varied if it is desirable to vary the way in which the bypassing tendons are wound around the endoscope. For example, the spaces 512' in FIG. 18C are oriented at an angle relative to the longitudinal axis of the vertebra, allowing the tendons to wind around the body of the endoscope as they project proximally. Furthermore, the tendon bypass spaces could be lubricated or composed of a lubricious material in order to facilitate free movement of the bypassing tendons across the segment, and prevent interference between the bending of the segment and the bypassing tendons.

FIGS. 18B and 18C show side views of the same vertebra as FIG. 18A. The two pairs of hinge joints 508, 506 are shown. Hinge joints 508, 506 are preferably located 90° apart and extend axially so that the hinge joints can pivotally mate with hinge joints from adjacent vertebrae. This mating 520 with adjacent vertebrae is more clearly seen in FIG. 18C. These hinges can be joined, pinned, or connected through the holes 525 as shown 522. Alternatively, hinges may also be made from materials utilizing, e.g., thermoplastics, shape memory alloys, etc. Once hinged, each vertebra can rotate relative to an adjoining vertebra in one axis. However, because vertebrae are hinged to each other in directions alternating by 90°, an assembly of multiple vertebrae is able to move in virtually any direction. The greater the number of vertebrae joined in this manner, the greater the range of motion. In one embodiment, two to ten vertebrae are used to comprise one segment, achieving a length of around 4 cm to 10 cm per segment. The dimensions of both the vertebrae and the binge joints can be varied, e.g., longer hinge joints will have a greater bending radius when joined to another vertebra. Furthermore, the number of vertebrae per segment can vary, e.g. more than ten vertebrae could be used.

Figure 18D:
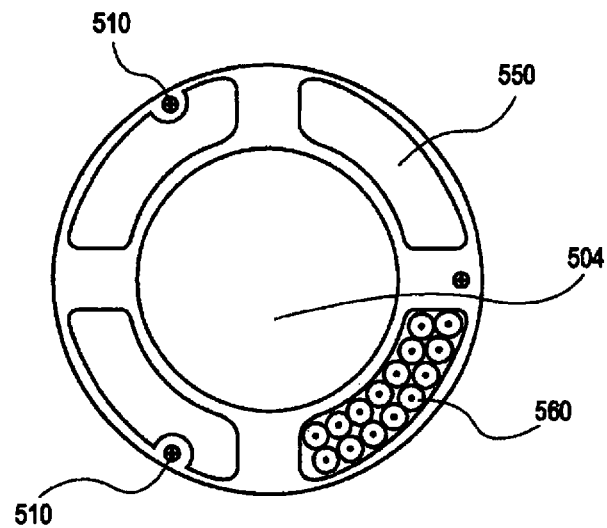
FIGS. 18D and 18E show a side view and a perspective view, respectively, of another embodiment of a vertebra-type control ring.
Figure 18E:
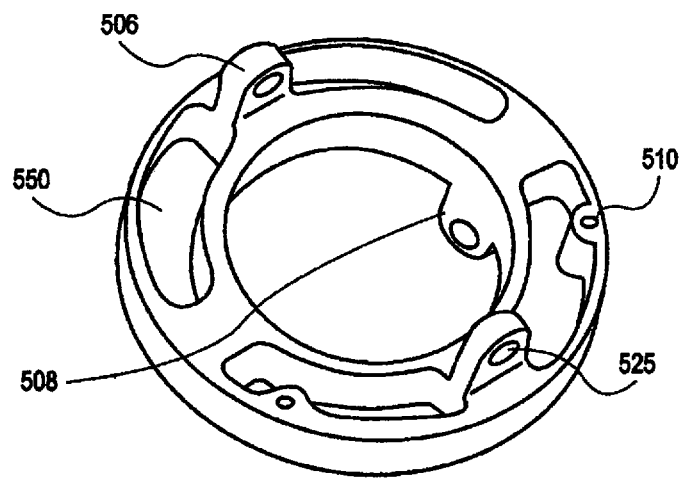

FIGS. 18D and 18E show another variation of a vertebra in sectional and perspective views, respectively. In FIGS. 18D and 18E, the tendons that bypass the segment may be contained within the body of the vertebra in a tendon bypassing space 550 rather than along the outer edge of the vertebra as shown in FIG. 18A. The vertebra of FIGS. 18D and 18E show four tendon bypassing spaces 550, and each space can hold approximately fifteen bypassing tendon sleeves. The number, shape and sizes of the tendon bypassing spaces can be varied. For example, a vertebra could have two tendon bypassing spaces that could hold more than thirty-five tendon sleeves. Moreover, the tendon bypassing space could also be located on the inside of the central aperture or lumen of the vertebra 504.

Although FIG. 18D shows tendon sleeves holding only a single tendon cable 560, more than one tendon cable could be contained in a tendon housing or sleeve. For example, if three tendons articulate a segment, all three tendons could be contained in a single tendon housing. Such a combined tendon housing could further utilize lubrication to accommodate independent movement by individual tendon cables and/or could be divided into compartments that isolate the tendons within the housing.

FIG. 18E also shows a perspective view of the hinge joints 506, 508 that can pivotally mate with pairs of hinge joints from adjacent vertebrae. Although FIGS. 18A and 18B shows two pairs of hinge joints projecting axially, a single hinge joint on each face of the vertebra could also be used. Moreover, as long as the binge joints can pivotally mate with adjacent vertebrae, the hinge joints can be located at different radial locations from the center of the vertebra. For example, the pairs of hinge joints shown in FIGS. 18A to 18C are located closer to the center of the vertebra than the hinge joints in FIGS. 18D and 18E.

Figures 19A, 19B:
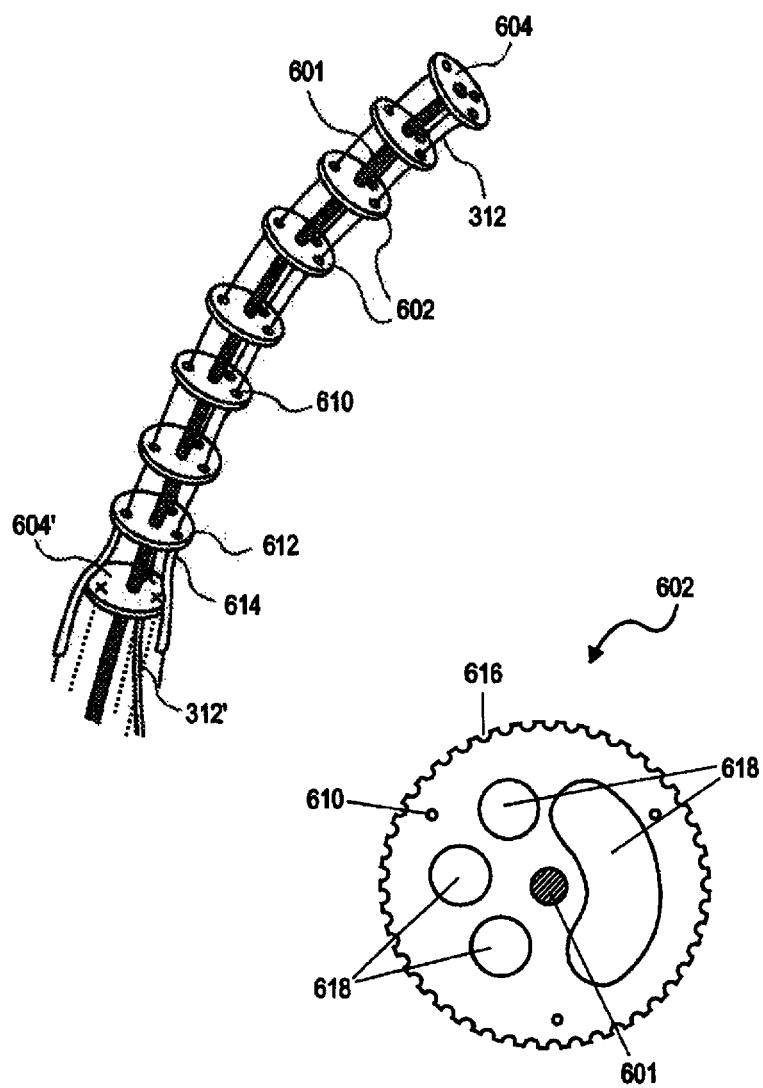
FIG. 19A shows a perspective view of an endoscope device variation with the outer layers removed to reveal the control rings and backbone.
FIG. 19B shows an end view of a variation of the control ring for an endoscope of the present invention.

FIGS. 19A and 19B illustrate a second variation of control ring. The variation shown in the figure utilizes a flexible backbone 601 preferably made of a material that is relatively non-compressible and non-extensible, to which control rings 602 are attached at intervals. This structure allows bending in a continuous curve in any desired direction. FIG. 19A shows a side view of one controllable segment of this variation with the outer layers removed to show the control rings and backbone. Multiple control rings 602 may be attached to the flexible backbone at regular intervals. Fewer or more control rings could be used to comprise a single segment depending upon the desired degree of articulation. The tendon cable 312 attaches to the most distal control ring of the segment 604. As with the vertebra-type variation, this central backbone embodiment is shown actuated by three tendons 310 attached at sites equally spaced around the edge of the most distal control ring of the segment 604. The tendon cables controlling the segment 312 pass through spaces or holes 610 defined in the control rings 602 through which they are free to move. These holes 610 could be lubricated, lined with a lubricious material or the control rings 602 may be composed of some lubricious material to facilitate cable motion through the holes 610. The tendon sleeve preferably attaches at a location 614 to the most proximal control ring in the segment 612. When a tendon 312 is placed under tension, this force is distributed along the entire segment. Because the inner tendon cable 312 is freely slidable within the tendon sleeve 314, and the tendon sleeve is fixed at both ends of the tendon 614, pulling on the tendon cable causes bending only in the selected segment.

FIG. 19A also shows the first control ring of a more proximal segment 604'. The tendons controlling the more distal segment may pass over the outside of the more proximal segments as they project proximally to the actuators. The outer edge of the control rings for the flexible backbone embodiment are shown with channels or tendon bypassing spaces 616 for bypassing tendons, as seen in FIG. 19B. As with the vertebra-type control rings, these tendon bypassing spaces could also be located within the control ring, for example, in an enclosed tendon bypassing space.

FIG. 19B shows an end view of control ring 602 which may be used with the flexible backbone embodiment of the endoscope. The center of the control ring contains a channel through which the flexible backbone 601 can be attached. A number of additional channels through the control ring 618 are also shown. These channels can be aligned with channels in neighboring control rings to form an internal lumen or channel for a fiber optic imaging bundle, illumination fibers, etc. as discussed above. Moreover, adjacent control rings may be spaced adjacently to one another at uniform or various distances depending upon the desired degree of bending or control. FIG. 19B shows three equally spaced holes 610 through which the tendon cable can pass; these holes 610 could also be used as attachment sites for the tendon cable, e.g., when the control ring is the most distal control ring in the segment 604, or for the tendon cable sleeve, e.g. when the control ring is the most proximal control ring in the segment 612. These holes 610 could be shaped specifically to receive either the tendon end or the tendon sleeve. Control rings of other designs could be used for different regions of the segment, or for different segments.

Figure 20A:
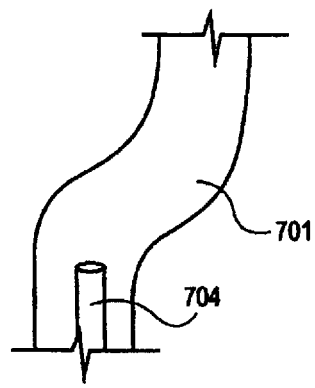
FIGS. 20A to 20C illustrate advancing the tendon driven endoscope of the present invention through a tortuous path.
Figure 20B:
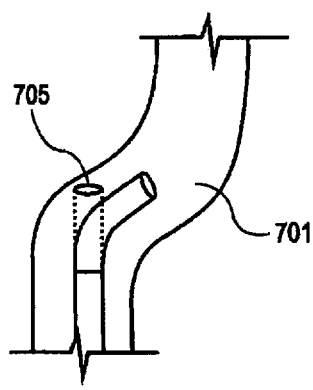
Figure 20C:
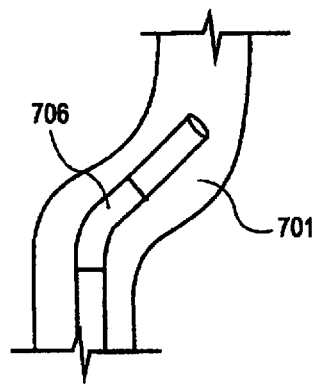

FIGS. 20A to 20C illustrate a variation of the tendon driven endoscope navigating a tortuous path. The path 701 is shown in FIG. 20A. This pathway may represent a portion of colon, for example. In FIG. 20A, the distal tip of the device 704 approaches the designated bend. FIG. 20B shows the distal tip being steered 705 to assume the appropriate curve. This steering could be performed manually by the user, e.g. a doctor, or automatically using an automatic detection method that could determine the proximity of the walls of the pathway. As described, the bending of the steerable tip is performed by placing tension on the tendon, or combination of tendons that results in the appropriate bending.

The device is then advanced again in FIG. 20C; as it is advanced, the selected curve is propagated down the proximal length of the endoscope, so that the bend of the endoscope remains in relatively the same position with respect to the pathway 701. This prevents excessive contact with the walls, and allows the endoscope to move more easily along the tortuous pathway 701. The endoscope is in continuous communication with the motion controller, and the motion controller can monitor the location of the endoscope within the pathway, e.g., depth of insertion, as well as the selected bends or curves that define the pathway of the endoscope. Depth can be determined by, e.g., the axial motion transducer 49 previously described, or by more direct measurement techniques. Likewise, the shape of each segment could be determined by the tension applied to the tendons, or by direct measurement, such as direct measurement of displacement of the tendon cables. The motion controller can propagate the selected shape of a segment at a specified location, or depth, within the body, e.g., by setting the lengths of the sides of more proximal segments equal to the corresponding lengths of the sides of more distal segments as the device is moved distally. The controller can also use this information to automatically steer the body of the endoscope, or for other purposes, e.g. creating a virtual map of the endoscope pathway for analytic use.

In addition to measuring tendon displacement, the motion controller can also adjust for tendon stretch or compression. For example, the motion controller can control the "slack" in the tendons, particularly in tendons that are not actively under tension or compression. Allowing slack in inactive tendons reduces the amount of force that is required to articulate more proximal segments. In one variation, the umbilicus at the distal end of the endoscope may contain space to allow slack in individual tendons.

The bending and advancing process can be done in a stepwise or continuous manner. If stepwise, e.g., as the tendon is advanced by a segment length, the next proximal segment 706 is bent to the same shape as the previous segment or distal steerable portion. A more continuous process could also result by bending the segment incrementally as the tendon is advanced. This could be accomplished by the computer control, for example when the segments are smaller than the navigated curve.

Figure 21:
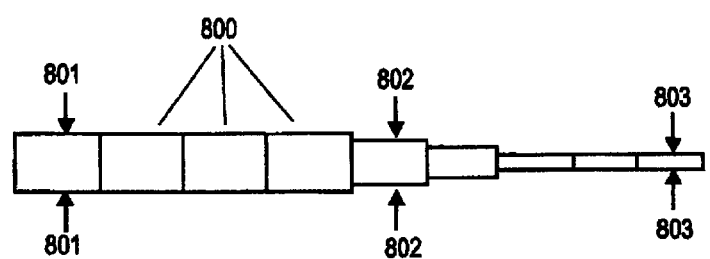
FIG. 21 shows a variation of the tendon driven endoscope of the present invention that has segments of differing diameters.
Figure 22:
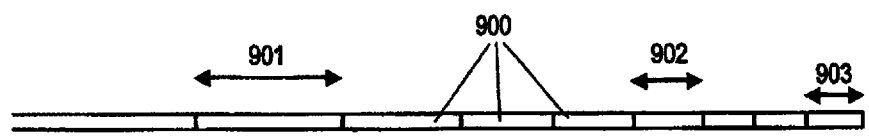
FIG. 22 shows a variation of the tendon-driven endoscope of the present invention that has segments of different length.

Controllable segments, including the steerable distal portion, can be selected to have different dimensions, e.g., different diameters or lengths, even within the same endoscope. Segments of different dimensions may be desirable because of considerations of space, flexibility and method of bending. For example, the more segments in an endoscope, the further it can be steered within a body cavity; however, more segments require more tendons to control the segments. FIGS. 21 and 22 illustrate two variations on tendon driven endoscopes.

FIG. 21 shows a tendon driven endoscope variation that has segments 800 of differing diameters. More distal segments may have a smaller diameter 803 than more proximal segments, e.g., 802, 801. The diameter of a typical endoscope could decrease from, e.g., 20 mm, down to, e.g., 12.5 mm. The endoscope shown in FIG. 21 appears telescoped, as the diameter decreases distally in a stepwise manner. This design would be responsive, e.g., to internal body structures that become increasingly narrow. This design would also help accommodate bypassing tendons from more distal segments as they proceed towards the proximal actuators because of the larger diameter of the more proximal segments. FIG. 21 shows four differently sized segments; however, virtually any number of differently sized segments could be used. Moreover, although the segments appear stepped in this variation, the outer surface may be gently tapered to present a smooth outer surface decreasing in diameter towards the distal end.

FIG. 22 shows another variation of the tendon driven endoscope that has segments of different lengths. Using segments of different lengths may require fewer overall segments 900 to construct an equivalent length of articulatable endoscope. As shown in FIG. 22, more proximal segments 901 are increasingly longer than more distal, e.g., 902, 903, segments. For example, segment length could be decreased from 20 cm at a proximal segment down to 6 cm at a distal most segment. The lengths may be decreased incrementally segment to segment by a constant factor; alternatively, lengths may be decreased geometrically, exponentially, or arbitrarily depending upon the desired articulation. In practice this results in an "averaging" of curves by more distal segments as bends and turns are propagated proximally. In order to accomplish this, the motion controller may be configured to accommodate the differently sized segments accordingly. Alternatively, endoscopes could be comprised of a combination of segments of different length and thickness, depending upon the application.

The tendons that articulate the segments are in mechanical communication with the actuators. However, it may be desirable to have the insertable distal portion of the endoscope be removable from the actuators and controller, e.g., for cleaning or disinfecting. A quick-release mechanism between the proximal end of the endoscope and the actuators is an efficient way to achieve an endoscope that is easily removable, replaceable or interchangeable. For example, the proximal ends of the tendons can be organized to allow predictable attachment to corresponding actuators. The tendons may be organized into a bundle, array, or rack. This organization could also provide other advantages to the endoscope, such as allowing active or passive control of the tendon slack. Furthermore, the proximal ends of each tendon can be modified to allow attachment and manipulation, e.g., the ends of the tendons may be held in a specially configured sheath or casing.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of endoscopically approximating tissue within a hollow body organ, comprising:
    positioning an elongated body adjacent to a portion of tissue to be excised from the hollow body organ;
    releasably gripping a first region of tissue circumferentially about a first tissue approximation component and a second region of tissue circumferentially about a second tissue approximation component, such that the portion of tissue to be excised is positioned between the first and the second tissue approximation components;
    actuating a cutting mechanism of the elongated body to cut a wall of the tissue to be excised, wherein the tissue is cut in a direction transverse to a longitudinal direction of the hollow body organ;
    approximating the first and the second tissue approximation components such that the first and the second regions of tissue are adjacent to one another; and
    fastening the first and second regions of tissue to one another.

2. The method of claim 1, wherein the first and second regions of tissue are both connected to the portion of tissue to be excised during the step of releasably gripping the first and second regions of tissue.

3. The method of claim 2, further comprising removing the tissue to be excised after the actuating the cutting mechanism so the first and second regions of tissue are not connected to one another by tissue of the hollow body organ.

4. The method of claim 1, wherein the approximating the first and the second tissue approximation components comprises longitudinally translating the first and the second tissue approximation components toward one another along the elongated body.

5. The method of claim 1, wherein the elongated body comprises a plurality of articulatable segments configurable to assume a selected shape along an arbitrary path when the elongated body is advanced distally or proximally, and wherein the method further comprises advancing the elongated body distally or proximally during the positioning of the elongated body.

6. A method of endoscopically approximating tissue within a hollow body organ, comprising:
    positioning an elongated body adjacent to a portion of tissue to be excised from the hollow body organ;
    moving a first tissue approximation component relative to the elongated body from a first position to a second position proximate to the portion of tissue and moving a second tissue approximation component relative to the elongated body from a first position to a second position proximate to the portion of tissue;
    releasably gripping a first region of tissue circumferentially about the first tissue approximation component by actuating a gripping mechanism of the first tissue approximation component when the first tissue approximation component is in the second position;
    releasably gripping a second region of tissue circumferentially about the second tissue approximation component by actuating a gripping mechanism of the second tissue approximation component when the second tissue approximation component is in the second position;
    removing the tissue located between the first and the second tissue approximation components while the first and second tissue approximation components are gripping the first and second regions of tissue, respectively;
    approximating the first and the second tissue approximation components such that the first and the second regions of tissue are adjacent to one another; and
    fastening the first and second regions of tissue to one another.

7. The method of claim 6, wherein actuating the gripping mechanisms of the first and second tissue approximation components comprises applying a vacuum force.

8. The method of claim 6, wherein actuating the gripping mechanisms of the first and second tissue approximation components comprises gripping the first and second regions of tissue with a plurality of attachment members.

9. The method of claim 8, wherein the attachment members are retractably positioned relative to the first and second tissue approximation components, wherein the actuating the gripping mechanisms of the first and second tissue approximation components comprises extending the attachment members relative to the first and second tissue approximation components.

10. The method of claim 8, wherein the attachment members comprise at least one of needles, hooks, and barbs.

11. The method of claim 6, wherein the releasably gripping of the first and second tissue regions comprise releasably gripping the first and second tissue regions by actuating gripping mechanisms disposed in circumferentially located ports of the first and second tissue approximation components.

12. The method of claim 6, wherein the removing the tissue comprises laparoscopically excising the tissue.

13. The method of claim 6, wherein the approximating the first and the second tissue approximation components comprises longitudinally translating the first and the second tissue approximation components toward one another along the elongated body.

14. The method of claim 6, wherein fastening the first and second regions of tissue to one another comprises stapling or suturing the first and second regions of tissue to one another.

15. The method of claim 6, wherein the elongated body comprises a plurality of articulatable segments configurable to assume a selected shape along an arbitrary path when the elongated body is advanced distally or proximally, and wherein the method further comprises advancing the elongated body distally or proximally during the positioning of the elongated body.

16. The method of claim 15, wherein the elongated body further comprises a steerable distal portion, wherein the advancing of the elongated body further comprises automatically controlling a proximal portion of the plurality of articulatable segments to assume a shape of the steerable distal portion.

17. The method of claim 16, further comprising controlling the automatically controlled proximal portion via an electronic motion controller during the advancing of the elongated body.

18. The method of claim 16, wherein the plurality of articulatable segments each comprise a plurality of vertebrae connected via hinges, and wherein the advancing of the elongate body further comprises pivoting the vertebrae relative to one another via the hinges.

19. The method of claim 6, wherein positioning the elongated body adjacent to the portion of tissue to be excised comprises positioning the elongated body adjacent to a portion of diseased tissue to be excised.

20. The method of claim 6, wherein the fastening comprises fastening the first and second regions of tissue to one another using a surgical stapler and a stapler anvil of the elongated body.

* * * * *